(12) United States Patent
Schnitta

(10) Patent No.: US 12,190,854 B2
(45) Date of Patent: Jan. 7, 2025

(54) SOUND DISTURBANCE INHIBITION SYSTEM

(71) Applicant: Bonnie S Schnitta, East Hampton, NY (US)

(72) Inventor: Bonnie S Schnitta, East Hampton, NY (US)

(*) Notice: Subject to any disclaimer, the term of this patent is extended or adjusted under 35 U.S.C. 154(b) by 594 days.

(21) Appl. No.: 17/373,670

(22) Filed: Jul. 12, 2021

(65) Prior Publication Data

US 2022/0031998 A1 Feb. 3, 2022

Related U.S. Application Data

(63) Continuation-in-part of application No. 16/521,568, filed on Jul. 24, 2019, now Pat. No. 11,081,096.

(60) Provisional application No. 62/702,780, filed on Jul. 24, 2018.

(51) Int. Cl.
*G10K 11/168* (2006.01)
*A61M 21/00* (2006.01)
*E04B 1/82* (2006.01)
*E04B 1/84* (2006.01)
(Continued)

(52) U.S. Cl.
CPC ....... *G10K 11/168* (2013.01); *A61M 21/0094* (2013.01); *E04B 1/82* (2013.01); *E04B 1/8209* (2013.01); *E04B 1/8218* (2013.01); *G10K 11/1752* (2020.05); *G10K 11/17861* (2018.01); *G10K 11/17873* (2018.01); *A61M 2021/0016* (2013.01); *A61M 2021/0027* (2013.01); *A61M 2021/0044* (2013.01); *A61M 2021/0061* (2013.01); *A61M 2205/42* (2013.01); *A61M 2250/00* (2013.01); *E04B 2001/8461* (2013.01);
(Continued)

(58) Field of Classification Search
CPC ........ E04B 1/82; E04B 1/8209; E04B 1/8218; E04B 2001/8461; A61M 2205/42; A61M 2250/00; A61M 2021/0027; G10K 11/168; G10K 11/1752
USPC ................................................. 181/198, 205
See application file for complete search history.

(56) References Cited

U.S. PATENT DOCUMENTS 2,337,885 A * 12/1943 Hallam ...................... E04H 1/14
52/145
2,736,928 A * 3/1956 Manning ................... E04H 1/14
D25/16
(Continued)

FOREIGN PATENT DOCUMENTS

DE 102014016397 A1 * 5/2016 ............. A47C 31/00
FR 3039001 A1 * 1/2017
GB 2501538 A * 10/2013 ........... A47B 83/001

*Primary Examiner* — Jeremy A Luks
(74) *Attorney, Agent, or Firm* — John F. Vadopia

(57) ABSTRACT

A partial enclosure for inhibiting sound passing into and out of the partial enclosure includes an absorber-barrier or an absorber-barrier-absorber, each made from sound absorbing material and sound barrier material and arranged to form the partial enclosure. The enclosure also includes an adaptive frequency matched sound-masking system. The absorber-barrier or absorbed-barrier-absorber is positioned to block or inhibit unwanted sound from various positions of a source of the unwanted sound, or motion of the source of the unwanted sound. The adaptive frequency matched sound-masking system includes a sound generating device arranged on or in the partial enclosure to emit anti-noise signal to cancel or inhibit the unwanted sound.

13 Claims, 22 Drawing Sheets

(51) Int. Cl.
*G10K 11/175* (2006.01)
*G10K 11/178* (2006.01)

(52) U.S. Cl.
CPC ............ *G10K 2210/118* (2013.01); *G10K 2210/3223* (2013.01); *G10K 2210/3224* (2013.01)

(56) References Cited

U.S. PATENT DOCUMENTS

| | | | | |
|---|---|---|---|---|
| 3,780,825 A * | 12/1973 | Rinaldi | ............... | G10K 11/16 5/512 |
| 5,123,874 A * | 6/1992 | White, III | ............ | E04B 1/34321 181/290 |
| 5,177,912 A * | 1/1993 | Ball | ................. | E04B 1/8218 52/36.2 |
| 6,382,351 B1 * | 5/2002 | Lastowski | ............. | E04B 1/86 119/168 |
| 6,446,751 B1 * | 9/2002 | Ahuja | ............... | A47H 23/02 181/290 |
| 7,377,078 B2 * | 5/2008 | Golino | ............... | A47B 87/00 108/50.01 |
| 7,690,158 B2 * | 4/2010 | Kelly | ................ | E04B 2/7429 52/794.1 |
| 8,136,626 B1 * | 3/2012 | Aliev | ................ | E04H 15/14 181/208 |
| 8,646,571 B2 * | 2/2014 | Aliev | ................ | H04M 1/19 181/198 |
| 9,523,191 B2 * | 12/2016 | Uetabira | ............. | G10K 11/168 |
| 9,624,718 B2 * | 4/2017 | Geller | ................ | A47B 13/00 |
| 9,856,643 B1 * | 1/2018 | Lytle | ................ | E04B 2/7405 |
| 2003/0067256 A1 * | 4/2003 | Stenftenagel | ......... | A47B 21/00 312/263 |
| 2007/0114892 A1 * | 5/2007 | Boxenbaum | .......... | A47B 51/00 312/223.3 |
| 2009/0056886 A1 * | 3/2009 | Shaw | .................. | E06B 3/80 160/368.1 |
| 2011/0185499 A1 * | 8/2011 | Richards | .......... | G10K 11/17873 381/388 |
| 2015/0269923 A1 * | 9/2015 | Ng | ..................... | H04R 1/1083 381/71.3 |
| 2016/0201318 A1 * | 7/2016 | Israel | ................ | G10K 11/162 181/290 |
| 2016/0232885 A1 * | 8/2016 | Schnitta | ............ | B32B 15/14 |
| 2016/0360899 A1 * | 12/2016 | Neveling | ............ | G10K 11/16 |
| 2017/0006367 A1 * | 1/2017 | Domash | ............ | A47C 7/727 |
| 2017/0055695 A1 * | 3/2017 | Carson | ............... | E04B 1/8218 |
| 2017/0284084 A1 * | 10/2017 | Carapinha | ........... | E04B 1/8409 |
| 2017/0358289 A1 * | 12/2017 | Israel | ............... | B32B 5/024 |
| 2018/0027316 A1 * | 1/2018 | Avliav | ............... | G10K 11/20 181/242 |
| 2018/0240451 A1 * | 8/2018 | Jeong | ............... | B32B 15/18 |
| 2018/0245334 A1 * | 8/2018 | Udagawa | ........... | F21S 8/06 |
| 2019/0017265 A1 * | 1/2019 | Jungbauer | ........ | G10K 11/168 |
| 2019/0117932 A1 * | 4/2019 | Luetje | ............... | A61M 21/0094 |

* cited by examiner

FIG. 6

SOUND DISTURBANCE INHIBITION SYSTEM

CROSS-REFERENCE TO RELATED APPLICATIONS

This application derives the benefit of the priority under 35 USC § 119(e) to U.S. Provisional Patent Application No. 62/702,780 filed Jul. 24, 2018, the content of which provisional application is incorporated herein by reference.

This application is a continuation-in-part of, and derives the benefit of priority to, U.S. patent application Ser. No. 16/521,568, filed Jul. 24, 2019 (now U.S. Pat. No. 11,081,096 issued Aug. 1, 2021), the content of which is incorporated herein by reference.

BACKGROUND OF THE INVENTION

The present invention is directed to a sound disturbance inhibition system that comprises an acoustic partial or quasi enclosure, for example, embodying a pillow, a curtain, tent, or canopy bed enclosure, other similar quasi-enclosure that is constructed to limit, i.e., inhibit sounds, such as snoring sounds, from entering and/or leaving the acoustic partial enclosure. Preferably, the inventive sound disturbance inhibition system includes an adaptive frequency matched sound-masking system, or subsystem, provided in or operatively coupled to the partial or quasi enclosure Sound disturbance inhibition systems are known, but have significant drawbacks. Known snore disturbance inhibition systems, such as a continuous positive airway pressure (CPAP) system, for example, either fully enclose the mouth or nose of the snorer and/or typically require a snorer to remain in a singular or restrictive positions. While these systems, when in operation significantly reduce the sounds of snoring, actually often make other sounds that may be disturbing, such as when there is not a full seal of the CPAP to the face of the snorer. For that matter, CPAP systems can become dis-lodged and their restrictiveness and lack of comfortability to the user limits their effectiveness under the most ideal conditions of use.

Other sound disturbance inhibition systems are known that attempt to inhibit or minimize the disturbance associated with snoring. For example, U.S. Pat. No. 8,325,934 B2 discloses an electronic system including a pillow unit encasing at least one error microphone and at least one loudspeaker in electrical connection with a controller unit. But there are drawbacks. For example, the pillow unit as disclosed does not have the capability of working alone to reduce the noise. That is, the pillow unit as designed always requires and relies upon the electronic system, regardless of the loudness of the snorer. The system essentially abates unwanted noise by first detecting the unwanted noise with a reference microphone, analyzing the unwanted noise, producing an anti-noise signal corresponding to the unwanted noise signal, all occurring in a pillow, thereby abating the unwanted noise. Unfortunately, the focus is not on the comfort of the person whose head is in the pillow and does not address issues such as the varying direction of the noise source, etc. For example, the anti-noise signal could be directed in one lateral direction, or directly up or at angle to the vertical, where the sounds from the snorer could be directed in the other lateral direction or at a different vertical angle upwards. Additionally, this known system does not appear to work until it has "learned" the disturbing unwanted noise or is pre-programmed with advanced knowledge of the variation of the unwanted noise, such as when the head turns. It follows that the sound that is desired to be inhibited must be present for some disturbing time until the system learns and correctly generates and transmits a proper anti-noise signal.

U.S. Pat. No. 5,844,996 discloses a system for attenuating noise which can be sensed by the auditory nerve. This known noise-attenuation system comprises a microphone positioned in a first sound region for sensing the noise present in the first sound region to reduce the sound in a second sound region. A problem with this known noise-attenuation system, however, is that it works in accordance with an error function and that to be effective, the microphone must sense and mathematically model the signal before it can create the error function. Hence, there is always the problem of the disturbance from the sound of the initial uncancelled signal(s) until the error function of the noise-attenuating system learns the signal and the last signal, after the speaker of the noise cancelling system sends the reverse phase signal after the source stops.

Perhaps as importantly, neither of these patents disclose means for saving a noise signal history, for example, including a user's medical information such as the user's noise sensitivity, and/or so that the system might rely on the user's noise signal history so that current noise signal conditions can in turn indicate a change in condition of health. When the noise of concern is a transient of varying loudness, it creates a learning problem for such conventional noise attenuation systems which varies in degree. In consequence, the efficacy of the system is reduced and often creates a secondary problem of transmitting a signal that did not previously exist.

As should be clear, the presence of such a previously non-existing signal is then another disturbing signal that can be greater in amplitude than the snore (or other un-wanted noise) signal it was generated to cancel, particularly where the audio speaker transmitting the anti-noise signal is closer to the person that is being disturbed than the actual noise source, e.g., a snoring wife or husband. Unfortunately, with motion of the person or person's head (an exemplary unwanted noise source) and variation of the source signal (variation of the disturbing unwanted noise, for example, throughout a particularly expressive snore/breathing cycle in which the loudness varies), the error function requires frequent adjustments. This raises yet another secondary complication/associated disturbance based on the changing signal, the error function, whereby the cancelling or anti-noise signal becomes continuous, resulting in a continuous transient noise problem.

SUMMARY OF THE INVENTION

The present invention overcomes the shortcomings of known arts, such as those mentioned above.

The invention provides an innovative sound disturbance inhibition system that inhibits the disturbance caused by the unwanted noise, such as from a person snoring, a person talking loudly in their sleep, an animal making sounds, etc., without restricting the position of the snorer, sleep talker, animal, or any other proximate "source" of disturbing, unwanted noise.

The inventive sound disturbance inhibition system comprises an acoustic partial or quasi-enclosure, for example, embodying a pillow, a curtain, tent, or canopy bed enclosure, other similar quasi-enclosure that is constructed to limit, i.e., inhibit sounds, such as snoring sounds, from entering and/or leaving the acoustic partial-enclosure.

Preferably, the inventive sound disturbance inhibition system includes an adaptive frequency matched sound-masking system, or subsystem, provided in or operatively coupled to the partial or quasi-enclosure. While the partial-enclosure may be formed in just about any shape, the materials from which it is formed preferably comprise an absorber-barrier material, or an absorber-barrier-absorber material, that is optionally collapsible/removable. For example, the acoustic material from which the partial-enclosure is formed may include a sound absorbing portion (such as a layer of sound absorbing material) and a sound barrier portion (such as a layer of sound barrier material). The sound absorbing layer may be positioned on the sound barrier layer, and vice versa. For that matter, the layers may be positioned on a base layer (attached, integral with or blended with the sound absorbing and sound barrier material). Also, the inventive acoustic material may comprise multiple sound absorbing layers, and/or multiple sound barrier layers, in any layer arrangement, with or without a base layer. For example, if there are 5 layers in total, in addition to the base layer, there can be 5-factorial or more possible layer arrangements, without deviating from the scope or spirit of the invention.

In an embodiment, the innovative sound disturbance inhibition system includes a frequency matched sound masking active noise cancellation system, which system or sub-system also preferably includes a pre-loaded database of sounds to which additional sounds fabricated as anti-noise signals may be added during intended operation. The sound masking active noise cancellation system/sub-system may be implemented using any known computer system that includes a computer controller, a memory sufficient to store computer-readable instructions and the pre-loaded database of sounds, etc., a sound pick-up device such as a microphone and a sound generating device such as a speaker or other sound transducer system. Preferably, the sound masking active noise cancellation system/sub-system is implemented as a set of computer readable instructions in a common smartphone, which includes sound pick-up, sound generation, memory storage, image pick-up, light signal generation, electronic signal communication and network adaptivity capability, both wired and wireless, in a single integrated unit. The sound signals in the pre-loaded database are utilized by the system to minimize the disturbance by the sound (to be cancelled), while the system is learning likely candidate sounds (preferably substantially equivalent to and 180 degrees out of phase with the sound to be cancelled), to support cancellation, to overcome this inherent short-coming of conventional anti-noise systems.

Hence, the innovative sound disturbance inhibition system includes two independent but complementary means for inhibiting noise, the mechanical system/sub-system in the form of the partial enclosure and the sound masking active noise cancellation system/sub-system, with its improved capability due to its reliance upon the pre-arranged stored anti-noise signals. The innovative sound disturbance inhibition system provides a perceptible improvement in noise reduction due to snorers, animal noises, and other disturbing unwanted sounds, even under circumstances where the sound masking active noise cancellation system/sub-system fails or is turned off, due to the quasi enclosure construction in reliance upon the sound absorbing and barrier-formed materials, as described above. That is, this noise reduction function without electronics is possible because the acoustic partial enclosure acoustically compensates for or dampens acoustic signals to reduce the noise/sound that passes through the partial enclosure to or from any nearby sound source, e.g., snoring person. Please note that the invention accounts for the case where the unwanted nearby sound source is a snoring person positioned in the partial enclosure, or alternatively, outside the partial enclosure, such that the partial enclosure minimizes sound to persons outside or inside the partial enclosure, respectively.

BRIEF DESCRIPTION OF THE DRAWINGS

The invention will be described in conjunction with the following drawings in which like reference numerals designate like elements and wherein:

FIG. 6 depicts an exemplary display image generated and presented to a user by the inventive method implemented in the adaptive frequency matched sound-masking system to effect registration, which like all display images and pre-recorded sounds, associated with the user or not, is stored in database that either is integrally part of the system of in communication with the system;

DETAILED DESCRIPTION OF THE INVENTION

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1A:
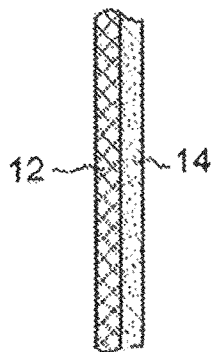
FIG. 1A depicts sheet material comprising a sound barrier layer and a sound absorptive or absorbing layer 14.
Figure 1B:
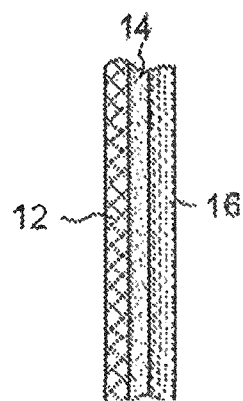
FIG. 1B depicts the FIG. 1A sheet material with a base layer arranged on the sound absorbing layer.
Figure 1C:
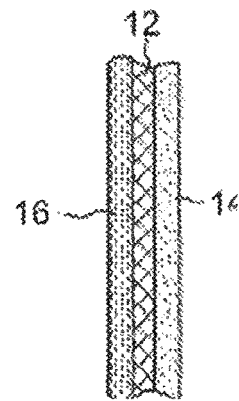
FIG. 1C depicts the FIG. 1A sheet material with a base layer arranged on the sound barrier layer.

In an embodiment, the inventive partial or quasi enclosure ("partial enclosure" and "quasi enclosure" are used interchangeably herein) is formed with a sheet acoustic material comprising a sound barrier layer 12 and a sound absorptive or absorbing layer 14, attached to or integral or blended with the sound barrier layer, such as shown in cross section in FIG. 1A. The sheet material also may include a base layer 16 attached to either the sound absorbing layer 14 or the sound barrier layer 12, as shown in FIGS. 1B and 1C, respectively. The sound absorbing layer operates to absorb sound where the barrier layer prevents sound from passing through, and may result in reflection.

Figure 1D:
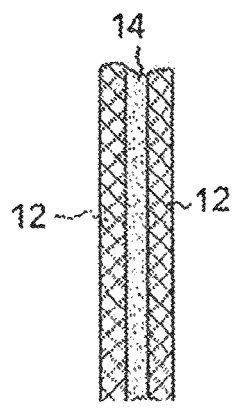
FIG. 1D depicts a barrier layer separated from a second barrier layer 12 by a sound absorbing layer.
Figure 1E:
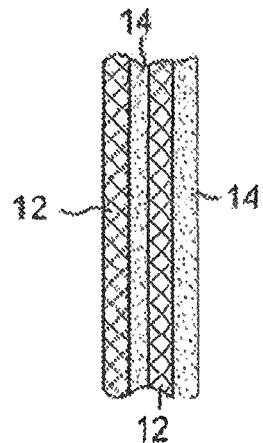
FIG. 1E depicts the sheet material of FIG. 1D with an additional sound absorbing layer on the second sound barrier layer.
Figure 1F:
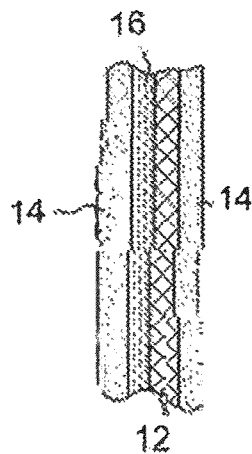
FIG. 1F depicts a base layer sandwiched between a sound absorbing layer and a barrier layer, where a second sound barrier layer is arranged on the barrier layer.
Figure 1G:
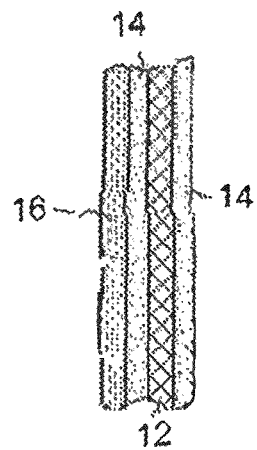
FIG. 1G depicts a base layer upon which a sound absorbing layer is arranged, with a sound barrier layer positioned on the sound absorbing layer and a second sound absorbing layer positioned on the sound barrier layer.
Figure 1H:
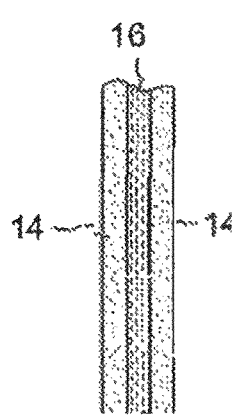
FIG. 1H depicts a base layer surrounded by two sound absorbing layers.

The sheet material used in the inventive partial enclosure may comprise multiple sound absorbing layers 14, and/or multiple sound barrier layers 12, in any layer arrangement, with or without a base layer 16. For example, if there are 5 layers in total, in addition to the base layer, there can be 5-factorial or more possible layer arrangements, without deviating from the scope or spirit of the invention. FIG. 1D, for example, shows the material sheet comprising a barrier layer separated from a second barrier layer 12 by a sound absorbing layer, where FIG. 1E shows the sheet material of FIG. 1D with an additional sound absorbing layer 14 on the second sound barrier layer, FIG. 1F depicts a sheet material with a base layer 16 sandwiched between a sound absorbing layer 14 and a barrier layer 12, where a second sound barrier layer 14 is arranged on the barrier layer. FIG. 1G shows a base layer 16 upon which a sound absorbing layer 14 is arranged, with a sound barrier layer 12 positioned on the sound absorbing layer 14 and a second sound absorbing layer 14 positioned on the sound barrier layer 12. FIG. 1H shows a simple arrangement with a base layer surrounded by two sound absorbing layers 14.

Please note that the barrier layer may exhibit sound barrier properties, for example, the base layer(s) 16 may limit sound passage, reflecting some sound, where the sound barrier layer(s) 12 prevent all sound from passing therethrough. Preferably, the base layer defines an aesthetic character of the partial enclosure, in the case where it is arranged as the outer layer and, depending on the application, any layer arrangement is possible, even a base layer with a single sound absorbing layer, or with a single sound barrier layer. For that matter, the sound absorbing material may be any type of material that absorbs or inhibits sound energy when sound waves pass by or through the material, as opposed to reflecting or channeling the sound energy, as is the case of a sound barrier. For example, LUMITEX® sound absorbing material, manufactured by or for, distributed and/or sold by SoundSense LLC, Wainscott, NY operates as an effective sound absorbing material. LUMITEX® is a lightweight, breathable, non-woven fabric that provides excellent acoustic absorption while requiring a fraction of the space required for traditional absorptive panels. And multiple layers of sound absorbing material, or one thicker layer, such as LUMITEX® may be used to form a laminate that operates as an excellent sound barrier/absorber.

A barrier on the other hand is governed by its ability to attenuate sound and has an STC rating, but typically not NRC. A barrier, such as a mass loaded vinyl (MLV), stops (depending on the density per square feet of the material) anywhere from 23 dB to 35 dB. The common MLV has a weight of one pound per square foot and an STC of 26. SoundSense LLC makes various sound barrier materials available. QB-111, for example, is a barrier/absorber formed as a multi-layer, quilted sound barrier that incorporates a mass loaded vinyl barrier septum with absorptive fiberglass decouplers on both sides. Likewise, QB-12 is a two-layer, mass loaded vinyl barrier with quilted absorptive fiberglass on one side.

Figure 2A:
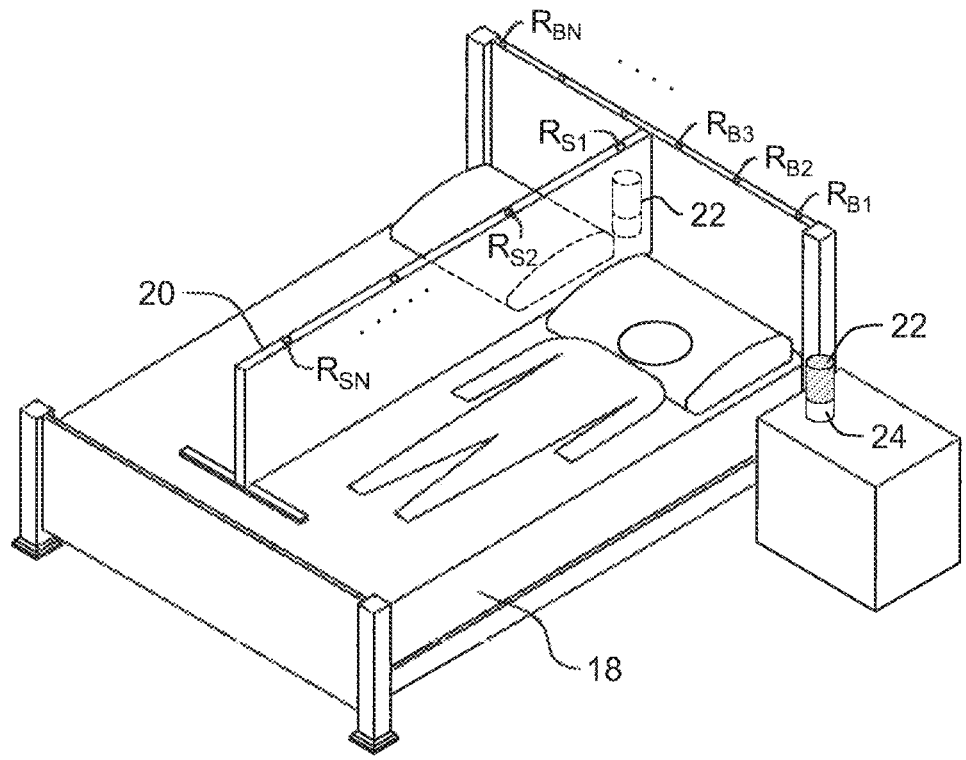
FIG. 2A depicts a plan view of a bed with a snorer, an embodiment of a barrier, which is in some sense a partial enclosure, formed with sheet material in accordance with the invention, two speakers and multiple receivers that are part of an adaptive frequency matched sound-masking system arranged in a tube that also houses one of the speakers.

FIG. 2A depicts a plan view of a bed 18 with a snorer S, a barrier 20, which is in some sense a partial enclosure, formed with sheet material in accordance with the invention, two speakers 22 and multiple receivers ($R_{B1}, R_{B2}, \ldots, R_{BN}, R_{S1}, R_{S2}, \ldots, R_{SN}$), and a controller 24 comprising a tube-like structure (that also includes one of the speakers), operating as a system, or subsystem, in accordance with a set of computer-readable instructions that are processed to implement an adaptive frequency matched sound-masking process of the invention, in cooperation with the physical barrier.

Figure 2B:
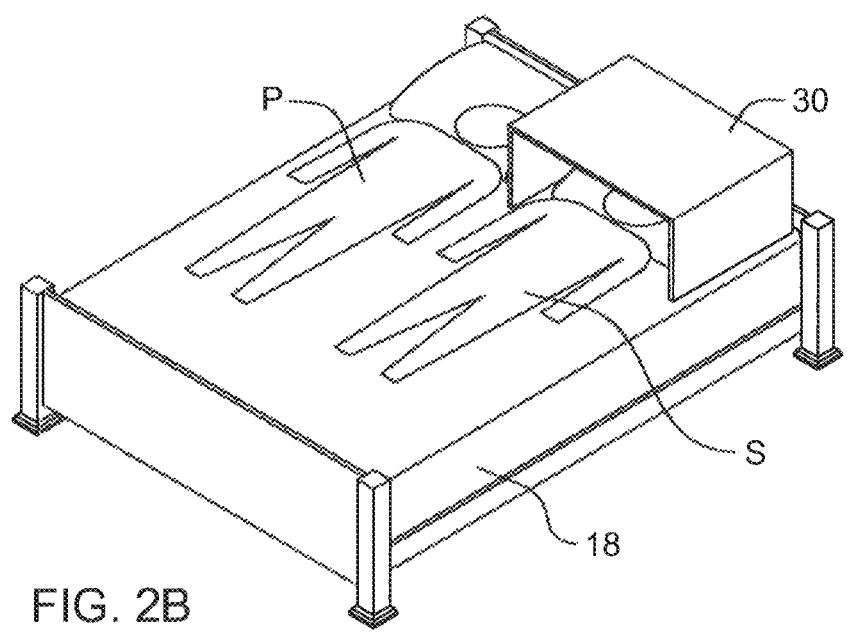
FIG. 2B depicts a partial enclosure formed in accordance with the invention.

FIG. 2B depicts a partial enclosure 30 formed in accordance with the invention, shown on a bed 18 and partially enclosing a snorer S, where next to the snorer is a person P who in this example is a non-snorer. The partial enclosure 30 is constructed with the sheet material formed as taught herein. Please note that inventive acoustic partial is easily collapsed or pulled aside for easy access and/or increased sound transmissibility in and out.

Figure 3:
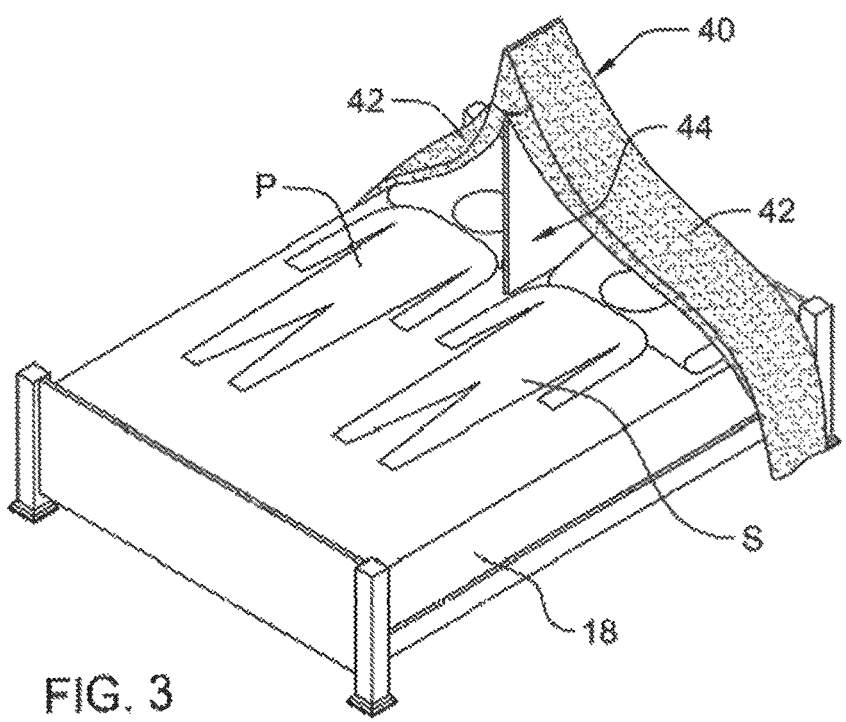
FIG. 3 depicts a partial enclosure, comprising a canopy-bed type arrangement, formed with curtains made of the sheet material and including at least one roller shade separating the persons depicted on the bed.

FIG. 3 depicts a partial enclosure 40, comprising a canopy-bed type arrangement (in bed 18), formed with curtains 42 made of the sheet material described herein and including at least one roller shade 44 that may be rolled up or down to separate the snorer S from the non-snoring person P.

Figure 4:
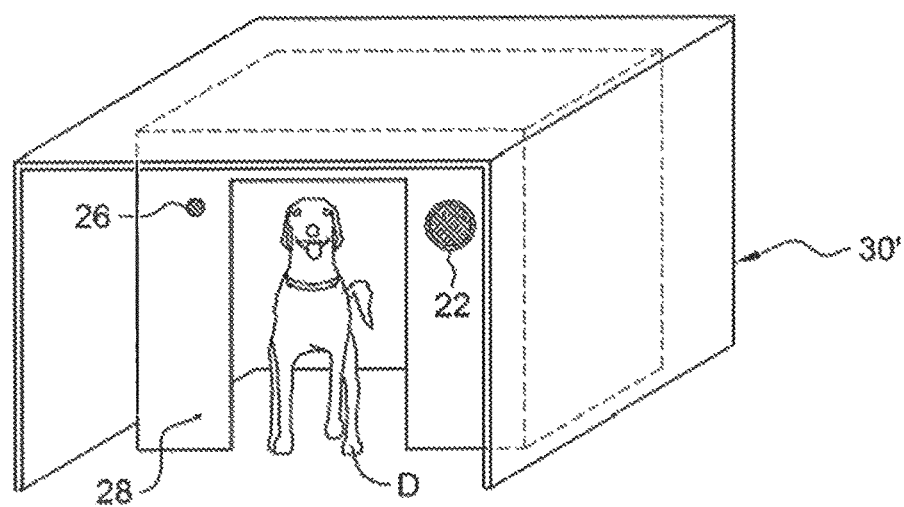
FIG. 4 depicts a dog (barking-ruff!) in a dog house surrounded by an inventive partial enclosure that includes a speaker and microphone of an adaptive frequency matched sound-masking system (where the controller is not shown)

FIG. 4 depicts another embodiment of an inventive enclosure 30' surrounding a dog house 28 in which a dog D is barking (ruff!). The doghouse 28 is surrounded by the inventive partial enclosure 30'. A speaker and microphone are arranged in the partial enclosure 30', which are part of an adaptive frequency matched sound-masking system. The system also includes a controller, in wireless communication with the speaker 22 and microphone 26, for controlling the adaptive frequency matched sound-masking system.

Figure 5A:
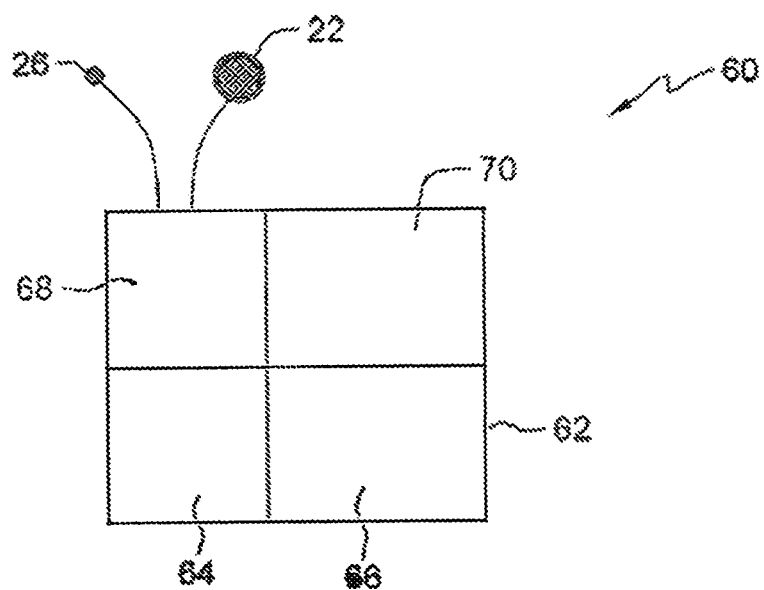
FIG. 5A depicts an embodiment of an adaptive frequency matched sound-masking system that can be used with the partial enclosure to form the sound disturbance inhibition system.

FIG. 5A depicts one embodiment of an adaptive frequency matched sound-masking system 60 of the invention. The adaptive frequency matched sound-masking system 60 includes a controller 62. The controller 62 includes a computer device 64 such as a microprocessor or microcontroller, a memory 66 that may be include ROM, RAM, an internal hard drive, or may connect to an external memory device physically or wirelessly, and operate to store computer readable instructions and operational data such as pre-recorded sounds and instantly recorded sounds and anti-noise signals; the memory 66 may operate as a database, in cooperation with the controller. The anti-noise signals are signals either pre-formed and stored in the memory, or downloaded to the memory, or instantly formed by the controller for use in cancelling unwanted noise. The anti-noise signals are 180 degrees out of phase with the electrical signals representative of detected unwanted sound signals (by the microphones), at or substantially at the frequency of the noise signals, which are presumed to be substantially periodic. Before sending the anti-noise signals to the speakers, the controller first determines the optimal magnitude, to control the optimum magnitude of the sound signal generated by the speaker in accordance therewith. The controller also includes an IO section 68 for communicating with the speaker(s) 22 and microphone(s) 26, and/or the Internet or other controllers or a bus if part of a network. While shown here connected physically to the speaker(s) and microphone(s), the controller and other system devices may operate wirelessly. Element 70 represents an input device and/or a displace device, for user control of the controller. Please note however, that while the inventive process of operating the system envisions user control, the system is configured to operate automatically on default, without need for user interaction.

Figure 5B:
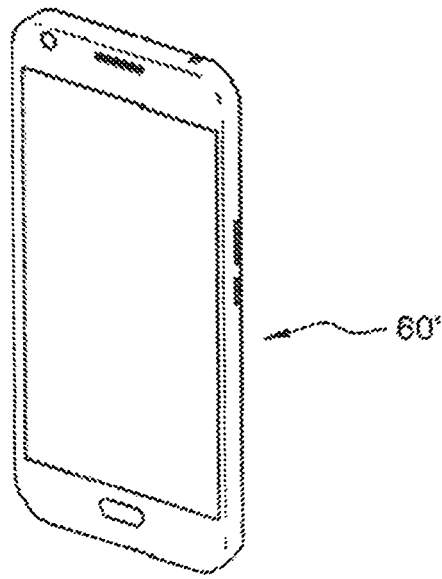
FIG. 5B depicts a smartphone that may include a set of computer readable instructions that when processed by a controller therein implement the inventive adaptive frequency matched sound-masking process.
Figure 5C:
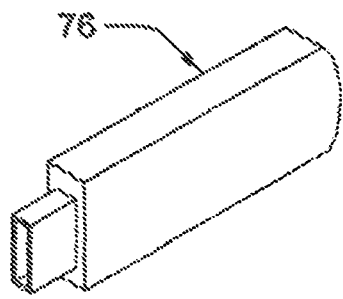
FIG. 5C depicts an exemplary computer readable medium, in a form of a portable memory storage device with a USB connector, for storing a set of computer readable instructions readily downloaded therefrom.

FIG. 5B depicts a smartphone 60' that may include a set of computer readable instructions that when processed by a controller therein implement the inventive adaptive frequency matched sound-masking process. FIG. 5C depicts an exemplary computer readable medium, in a form of a portable memory storage device with a USB connector 76, for storing a set of computer readable instructions readily downloaded therefrom. For that matter, a database with preformed anti-noise signals, or prior known user signals may be maintained in the computer readable medium. For that matter, the computer readable medium may be any memory device that is wired or wirelessly connectable to the system 60 and/or controller 64.

Preferably, the system 60 is utilized with a partial enclosure or barrier constructed with the sound absorptive/sound barrier material, as described. Most preferably, the system 60 is implemented in a smart phone uploaded with a set of computer readable instructions that when processed by a controller in the smartphone implement the adaptive frequency matched sound-masking method. In addition to the computer readable instructions for implementing the inventive process, however, several instructions also are included for controlling the smartphone to go directly to voicemail, without "ringing," when the smartphone is in its operational state as the adaptive frequency matched sound-masking system. For that matter, operation of the frequency matched sound masking and/or active noise cancellation system, in reliance upon the large data set of pre-recorded sounds of concern, also may be activated by either a facial recognition system that notes the mouth opening for a snore, an error function increase or detection from the active noise cancelling system (the system implements an error correcting loop with negative feedback to generate the corrected frequency for the anti-noise signal), or similar event detector that reduces the learning time of the frequency matched sound masking or active noise cancelling system. As such, the system overcomes the problems that occur for machine learning of an event and specifically a transient event and the motion of the source to be cancelled and/or masked, such as ahead turning or mouth position moving.

So, while the inventive enclosure alone can overcome the problems associated with unwanted sound, and/or a source position and motion of the source such as from a snoring person (e.g., sleeping snoring person rolling over), an animal moving, a moving vehicle emitting a sound such as from its engine or from a sound source such as a siren arranged on the vehicle, etc., implementation of the adaptive frequency matched sound-masking system to complement the physical enclosure optimizes the noise inhibition. And the use of the adaptive frequency matched sound-masking system with the partial enclosure, as an inventive A sound disturbance inhibition system provides for at least two options which increase the efficacy of the partial enclosure.

The first option is positioning the adaptive frequency matched sound-masking system not necessarily close to the noise source, but closer to the potentially disturbed person (such as the snorer's partner) If the unwanted sound source is a snoring person, the sound masking implemented by the adaptive frequency matched sound-masking system is specifically directed to the frequencies of the snore. Likewise, if the disturbing sound is a person talking in their sleep, then the adaptive frequency matched sound-masking system generates sounds having frequencies that are similar or related to the frequencies generated by the person talking, but out of phase to effect cancellation.

This sound masking can begin over a frequency range that is chosen from the database and then over a frequency range that the system "learns." In the preferred embodiment, the database is one that is known to match the snorer, talker, animal sounds, etc.

Another option that overcomes the problems of source position, source movement or noise disturbance while the adaptive frequency matched sound-masking system learns the error function for the noise cancellation or masking, is that it includes an adaptive autoregressive ("AR") function, or auto regressive moving average (ARMA) function. Please note that in any implementation, most if not all of the microphones and speakers are arranged in the inventive partial enclosure. The optional active noise cancellation system works not only with a memory-stored set of sound signals (e.g., snore or other disturbing unwanted noise signals), but also is capable of learning and refining the signal based on changing noise signature (frequencies and/or amplitude) or position of the source. As an example, the unwanted sound (e.g., snore) signal may start out as a simple sine wave of frequency 250 Hertz. When the person goes to bed they say, "going to bed". There is a short time when there is no snoring, but just the background noise. Then, as soon as the system detects a change in the background (an event that is the snore), it immediately generates the reverse phase 250 Hertz (i.e., the anti-noise or masking signal), and outputs it to the speaker to generate the physical cancelling sound signal. The actual signal representative of the selected sound is then compared to the database 250 Hertz signal and changed, if necessary, for the next signal. This trigger to begin the active noise cancelling system can be an active user fed command, input through a Graphical user interface (GUI) or downloaded via the controller 62 or a remote computer in electrical communication with the remote computer, an active face recognition system that "knows" when the head is on a pillow and the mouth opens (such as captured by an image pick-up device or camera that is part of the adaptive frequency matched sound-masking system as implemented), a passive system that "listens" for the first snore, etc., without limitation.

Both the adaptive frequency matched sound masking and/or the active noise cancelling systems obtain the initial sound or sounds in the large database based on preliminary identifiers, such as facial recognition, speech signatures, breathing or trigger sounds, etc. This unique trigger can take into account the position of the head, as well as the degree to which the mouth is open or the movement of the chest. The full system can be an app on a phone with certain portions in a cloud, part of an audio assistant, an iPad or any other data processing system, including a computer, and any combination thereof.

Figure 6:
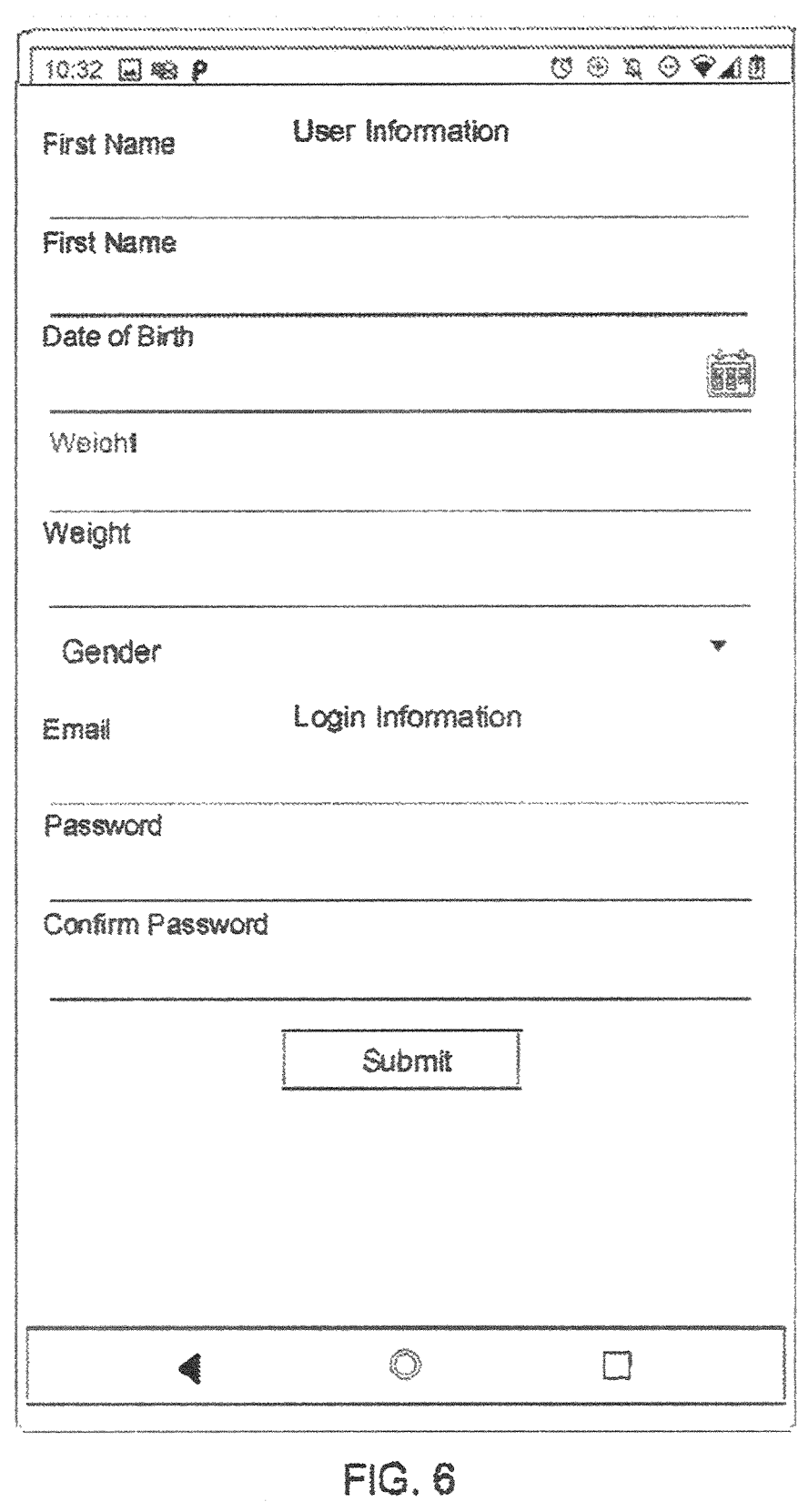

FIGS. 6-13 together depicts operation of the adaptive frequency matched sound-masking system, when it is not configured for wholly automatic operation. FIG. 6 depicts an exemplary display image generated and presented to a user by the inventive method implemented in the adaptive frequency matched sound-masking system to effect registration, which like all display images and pre-recorded sounds, associated with the user or not, is stored in database that either is integrally part of the system of in communication with the system.

Figure 7:
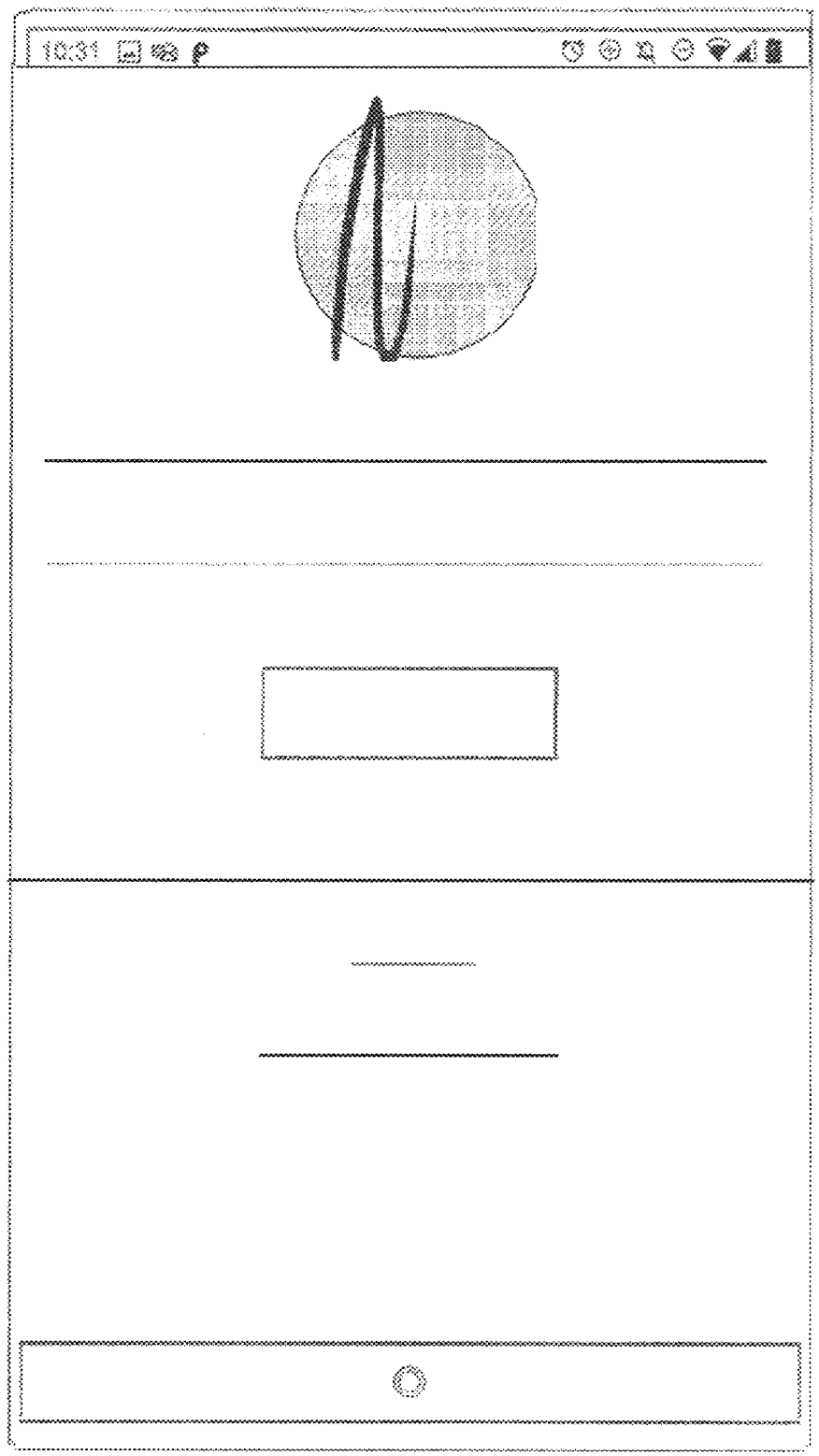
FIG. 7 depicts an exemplary display image of login screen presented to a user by the inventive method during intended use.
Figure 8:
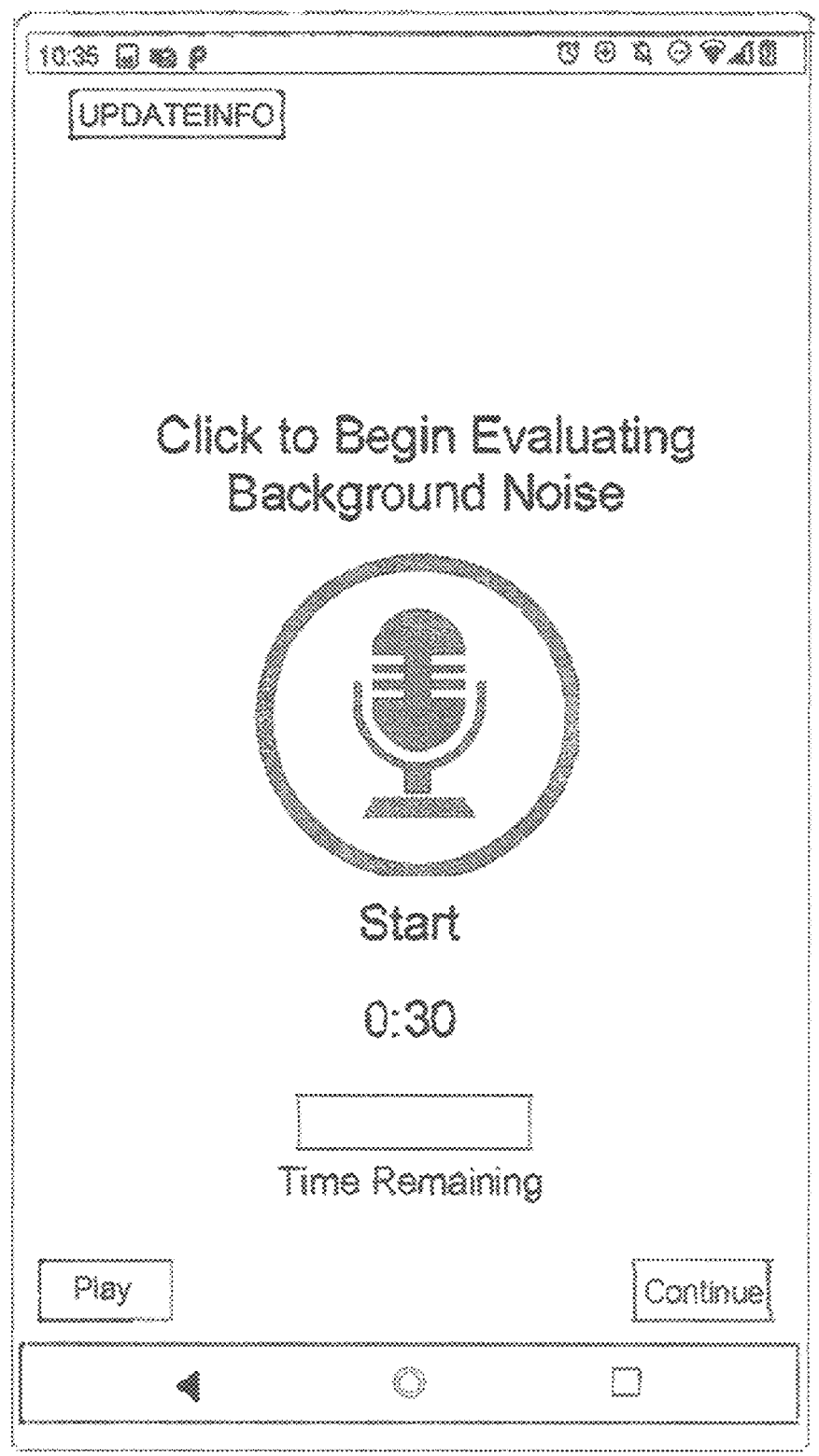
FIG. 8 depicts an exemplary display image presented to a user by the inventive method that allows the user to start recording background noise in order to process to cancel the background noise or store the background noise signal for future use, for example, a snore signal.
Figure 9:
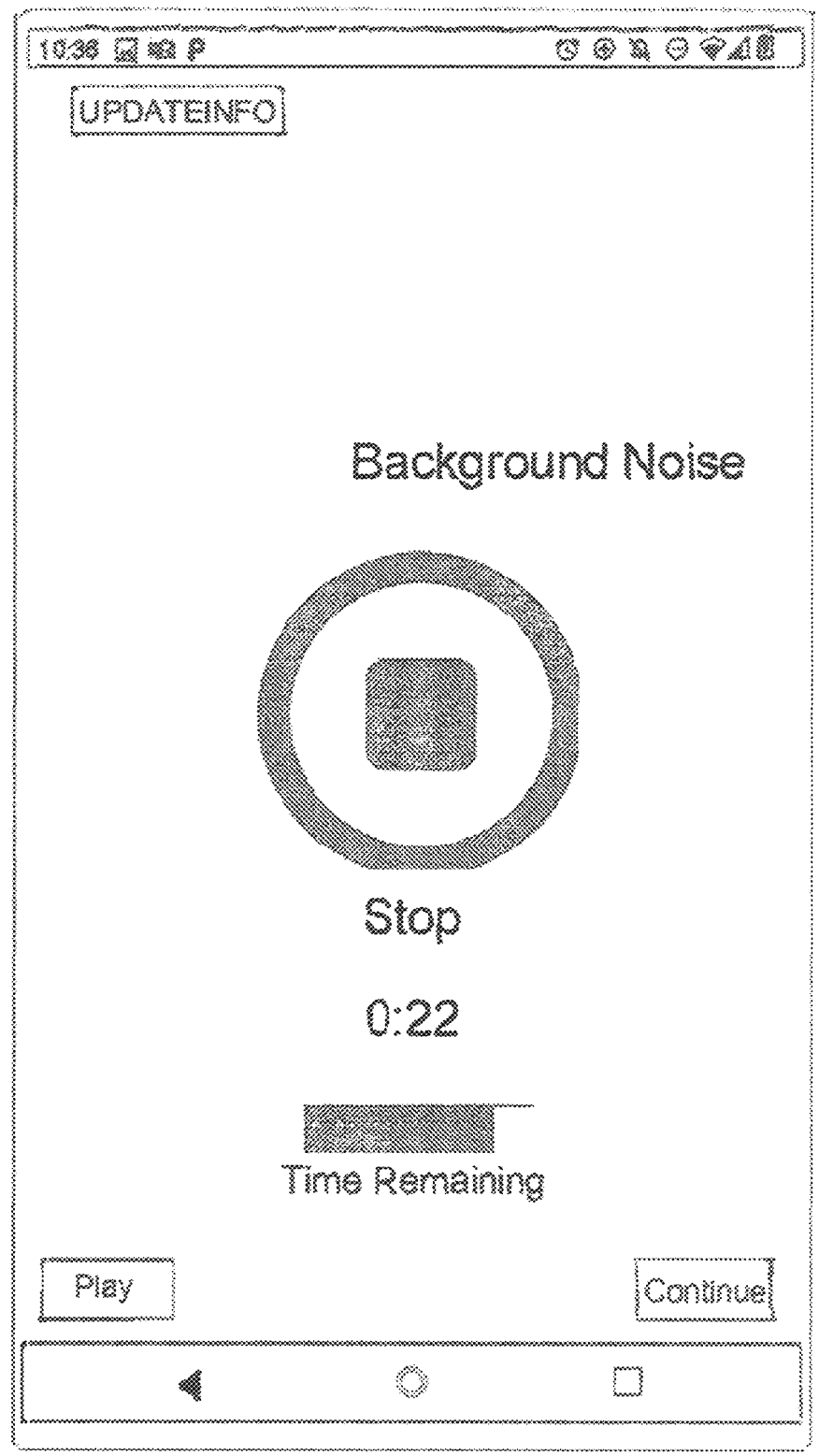
FIG. 9 depicts an exemplary display image presented to a user by the inventive method that lets the user know that the system is recording the background noise.
Figure 10:
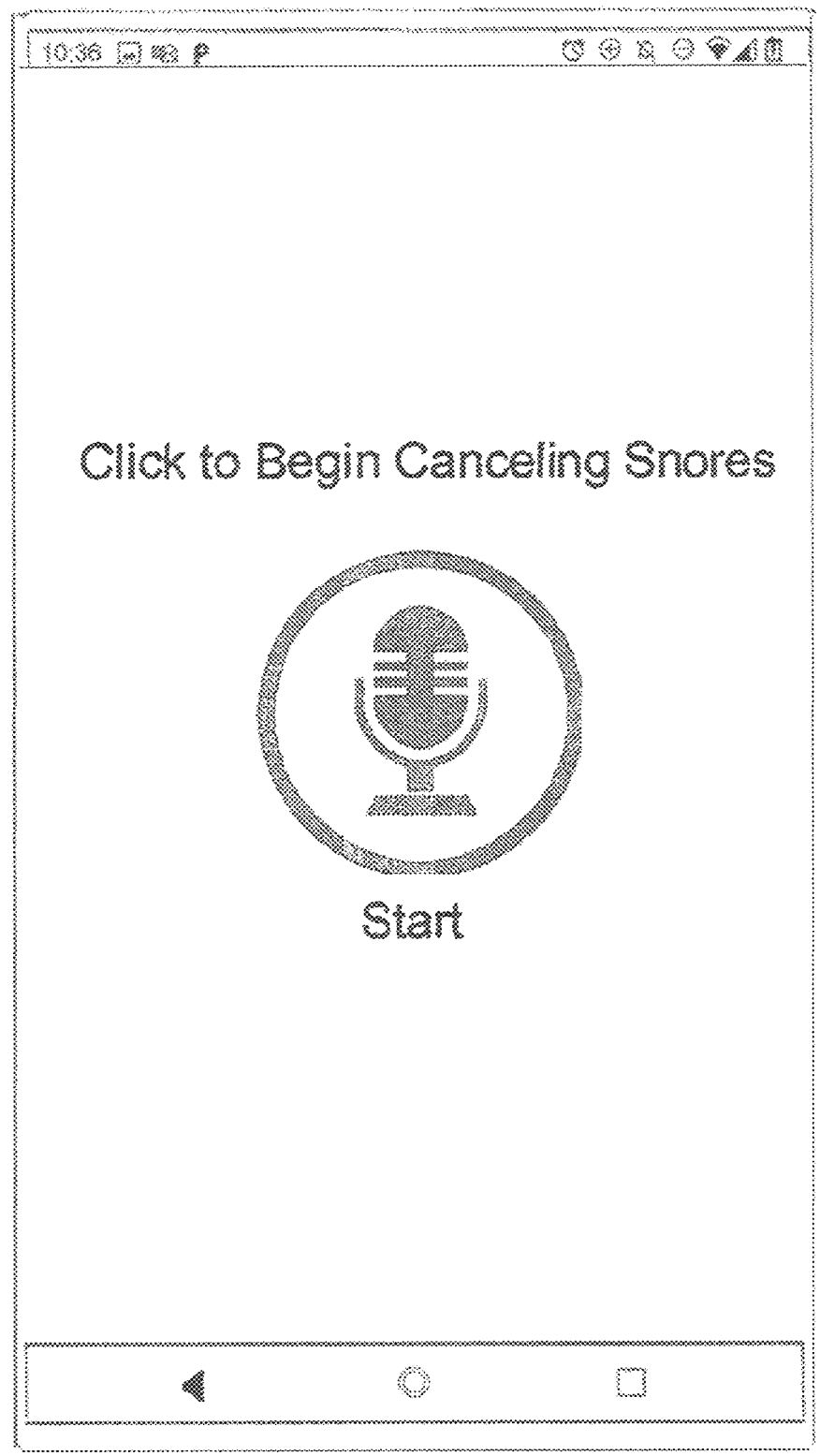
FIG. 10 depicts an exemplary display image presented to a user by the inventive method that lets the user start cancellation, in a system embodiment that is configured for user control of the inventive method, rather than the default configuration where all processing is automatic.

FIG. 7 depicts an exemplary display image of login screen presented to a user by the inventive method during intended use, while FIG. 8 depicts an exemplary display image presented to a user by the inventive method that allows the user to start recording background noise in order to process to cancel the background noise or store the background noise signal for future use, for example, a snore signal. FIG. 9 depicts an exemplary display image presented to a user by the inventive method that lets the user know that the system is recording the background noise, and FIG. 10 depicts an exemplary display image presented to a user by the inventive method that lets the user start cancellation, in a system embodiment that is configured for user control of the inventive method, rather than the default configuration where all processing is automatic.

Figure 11:
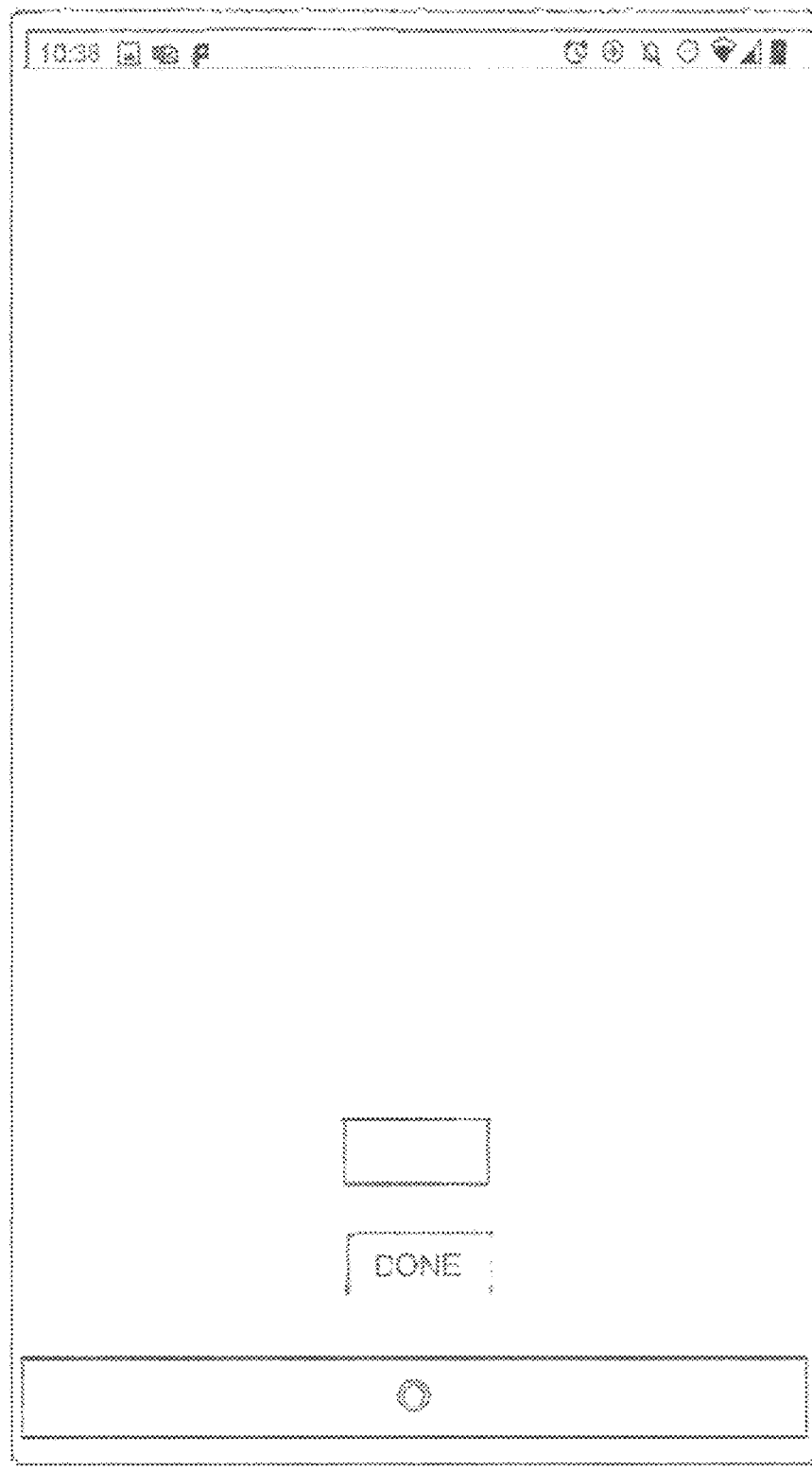
FIG. 11 depicts an exemplary display image presented to a user by the inventive method that lets the user stop cancellation, in a system embodiment that is configured for user control of the inventive method, rather than the default configuration where all processing is automatic.
Figure 12:
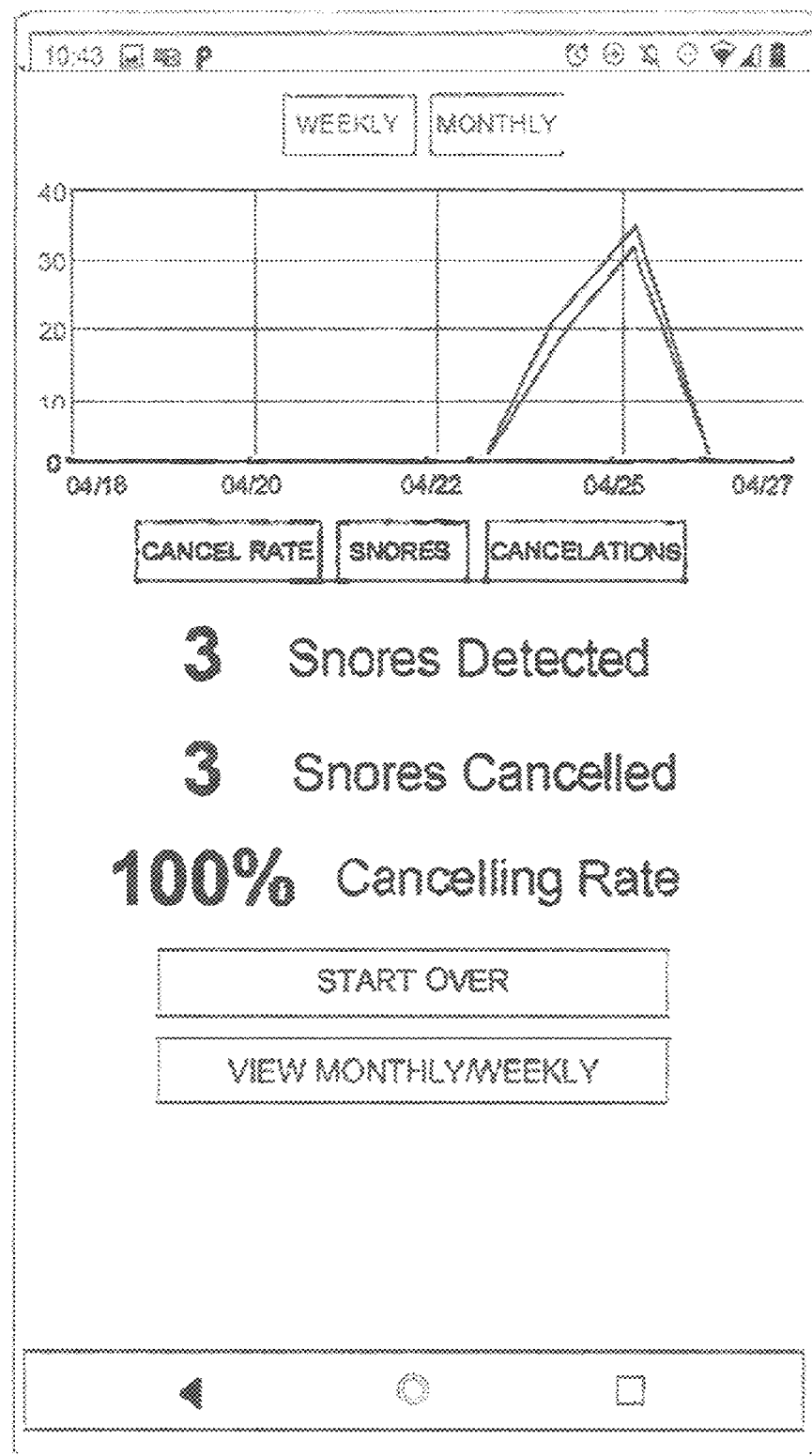
FIG. 12 depicts an exemplary display image presented to a user by the inventive method embodying a weekly dashboard memorializing system operation.
Figure 13:
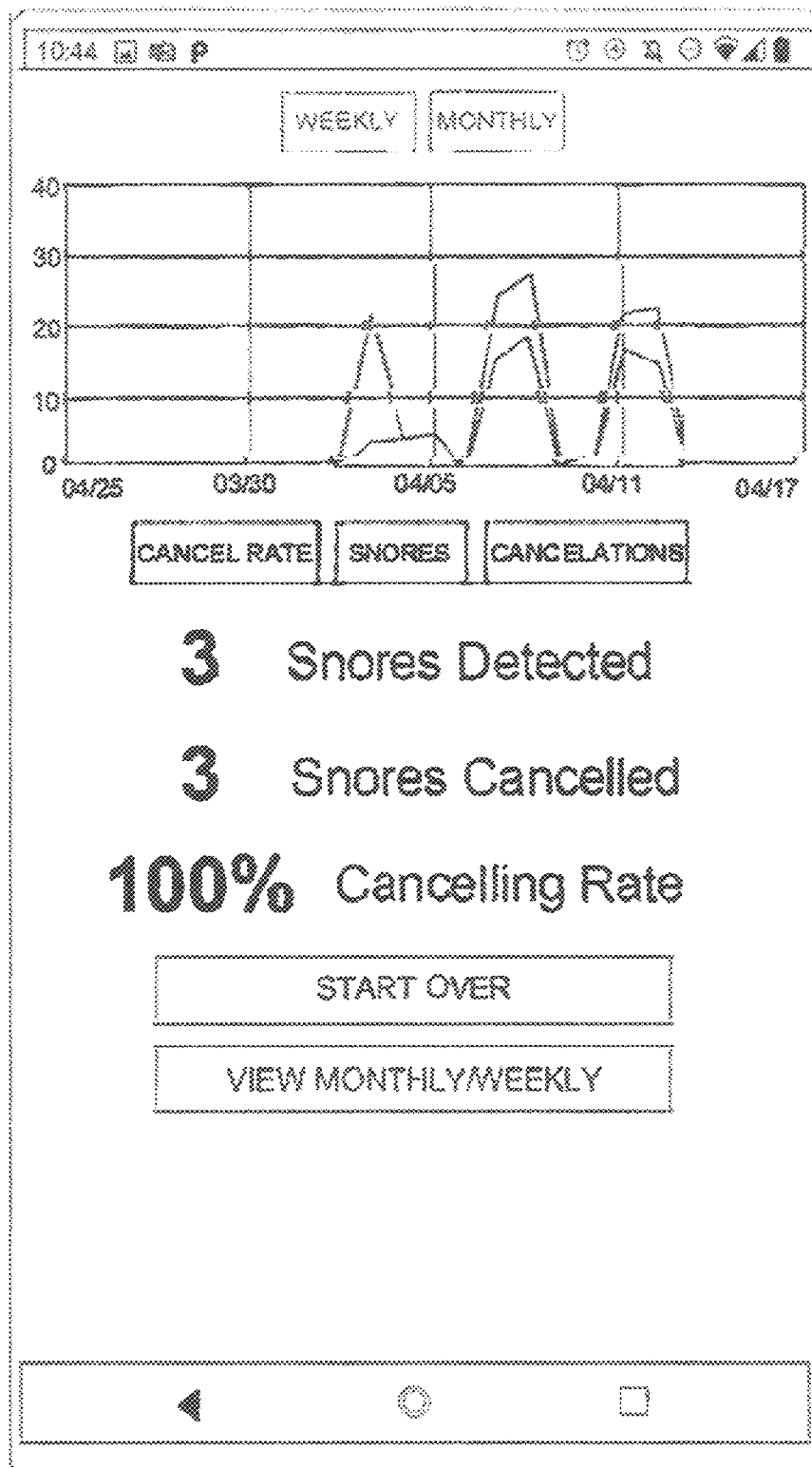
FIG. 13 depicts an exemplary display image presented to a user by the inventive method embodying a monthly dashboard memorializing system operation.

FIG. 11 depicts an exemplary display image presented to a user by the inventive method that lets the user stop the noise cancellation process, in a system embodiment that is configured for user control of the inventive method, rather than the default configuration where all processing is automatic. FIG. 12 depicts an exemplary display image presented to a user by the inventive method embodying a weekly dashboard memorializing system operation and FIG. 13 depicts an exemplary display image presented to a user by the inventive method embodying a monthly dashboard memorializing system operation.

It has become increasingly important to be able to make one's office portable, as well as a sleep or nap environment. In this same line of growing daily requirements for adaptable essential operational acoustic needs is the necessity to minimize disturbing noise. Whereas the embodiments discussed above are focused on providing quietude and making the partial enclosure something that could easily be transported, other embodiments are intended to make the partial enclosure even more portable, while maintaining its acoustic efficacy, as depicted in FIGS. 14A-G, 15A-B, and 16-17. What is shown in those figures is a partial enclosure 140 having a collapsible clamshell shape, having a frame 145 formed of semicircular ribs 141 joined at hinges 142, a base 143, and including a sheet 144 of at least one of an absorber material, and an absorber-barrier material, in which a user could easily expand. The absorber material with sufficient transmission loss would be the version of the product for increased quietude, while the absorber-barrier material is for the product version that is used to maximize the inhibition of noise entering or exiting the partial enclosure given the theoretical constraints associated with the fact that it is not a full enclosure, although an embodiment could be constructed with both a sheet of absorber material and a sheet of absorber-barrier material. Sheet 144 may also be formed as described above with reference to FIGS. 1A-1G. Sheet 144 may also have a finishing fabric (not shown) on the inside surface, outside surface, or both. Frame 145 may have handles 146, as shown in FIGS. 14D-G and 15B, for ease of transport. Base 143 may also be formed of one or more of the materials used to form sheet 144, or a cushion to act as a pillow, a vibration pad, such as a high durometer pad, to prevent vibrations from the unwanted sound being felt on the inner surface of 143, including but not limited to a foam for general comfort. Base 143 and sheet 144 may be removably detachable from frame 145, or may be permanently affixed thereto.

Figure 14A:
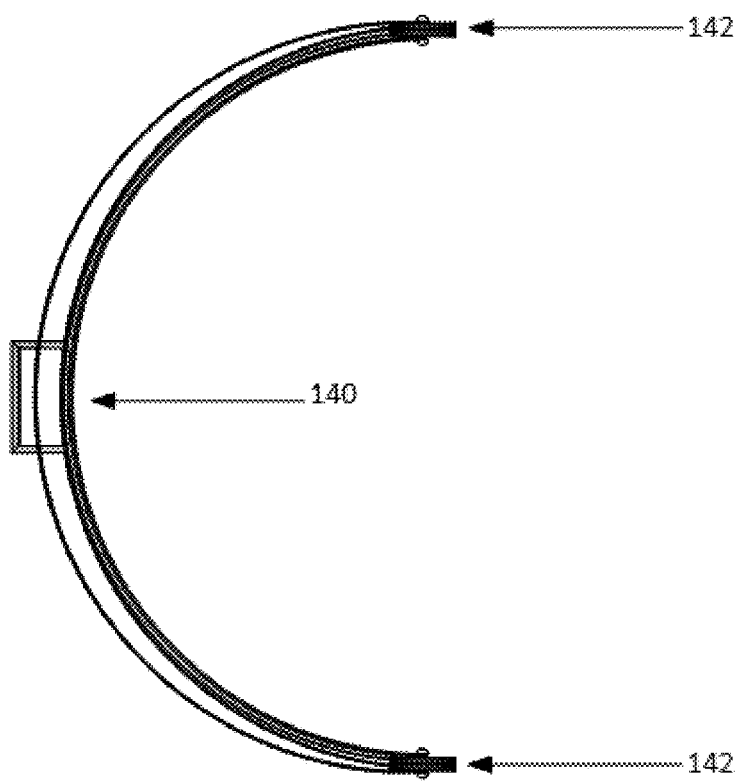
FIG. 14A depicts a top view of a clamshell embodiment of the noise reducing system of the present invention in an open position.
Figure 14B:
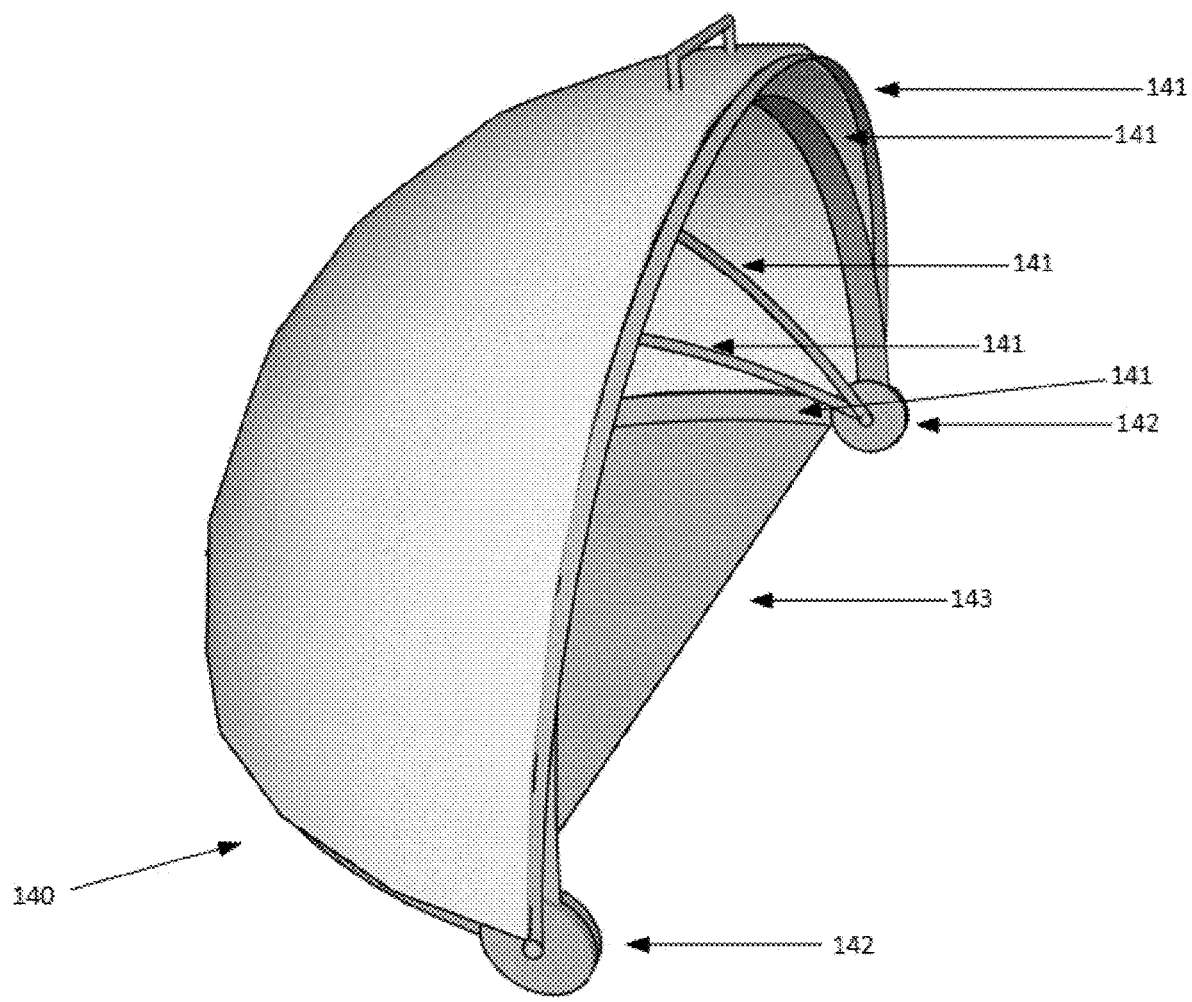
FIG. 14B depicts a perspective view of a clamshell embodiment of the noise reducing system of the present invention in a partially closed position.
Figure 14C:
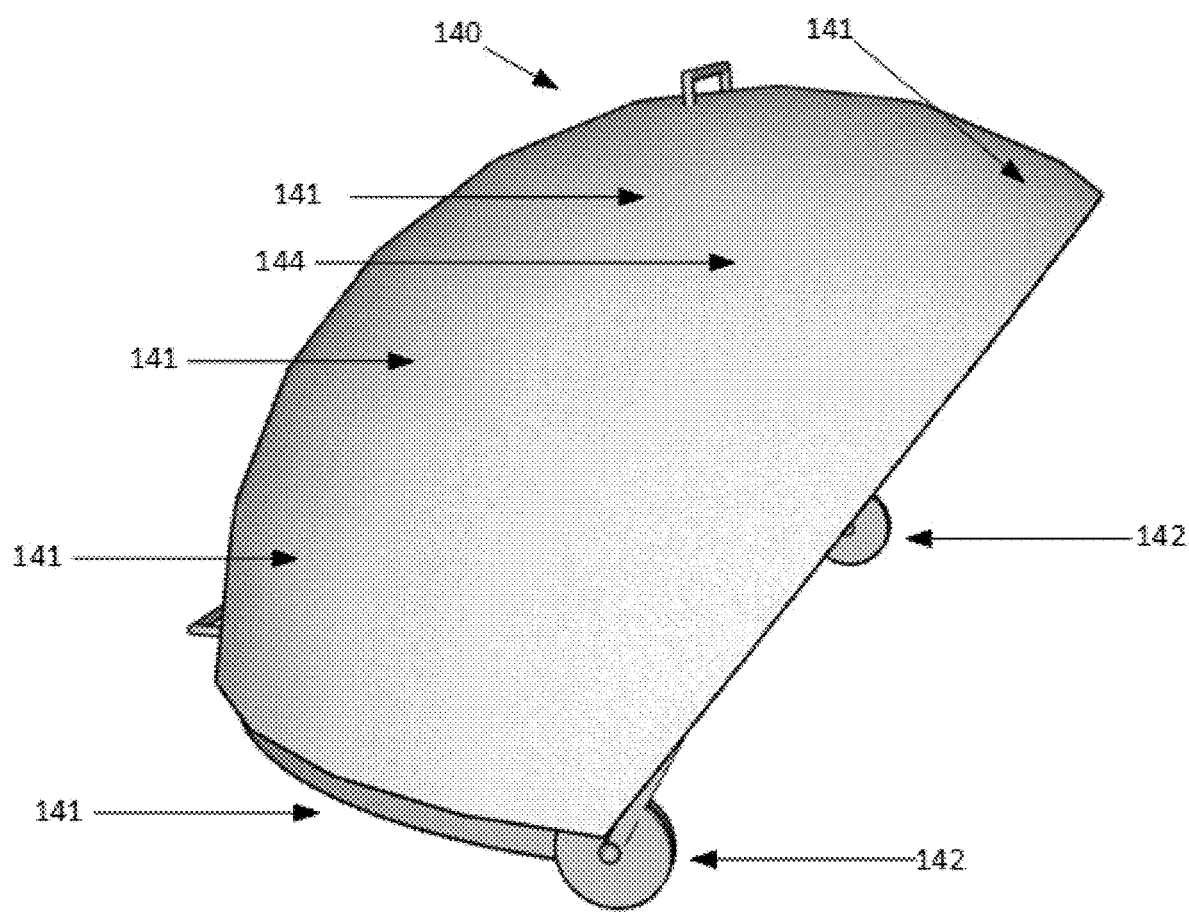
FIG. 14C depicts a perspective view of a clamshell embodiment of the noise reducing system of the present invention in a fully closed position.
Figure 14D:
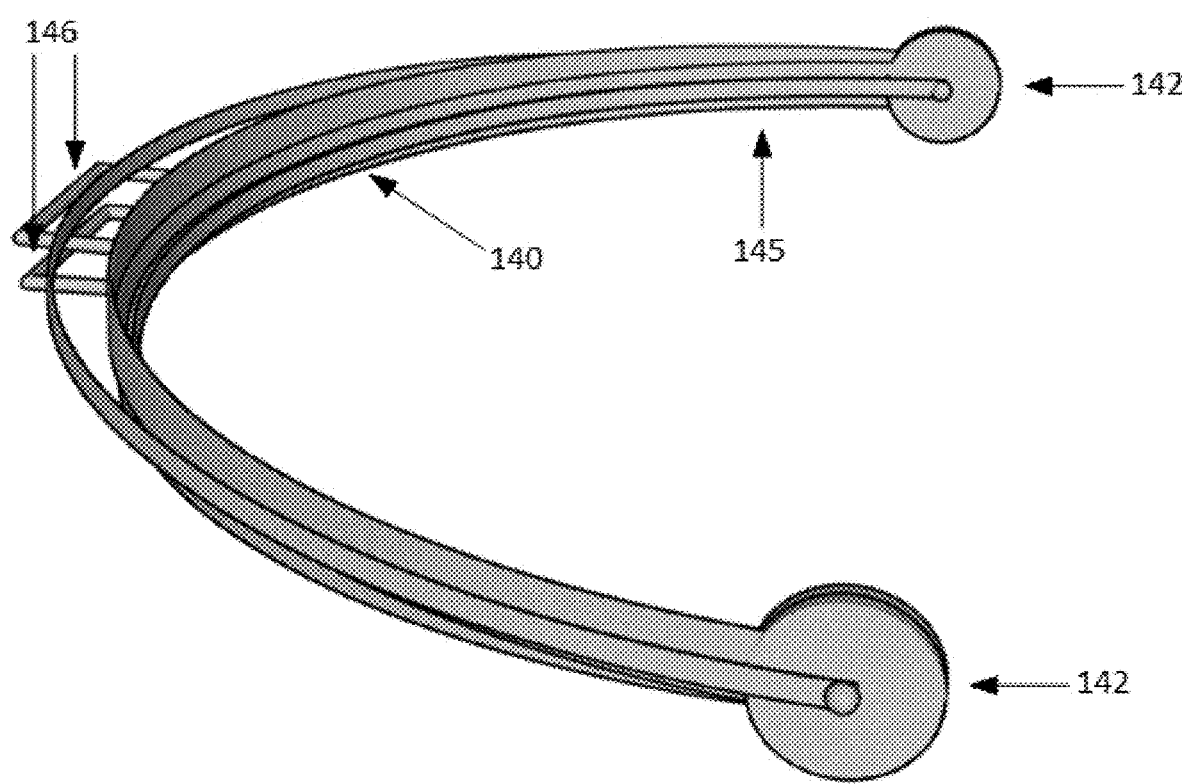
FIG. 14D a photograph of an example embodiment of the frame of a clamshell embodiment of the noise reducing system of the present invention in an open position.
Figure 14E:
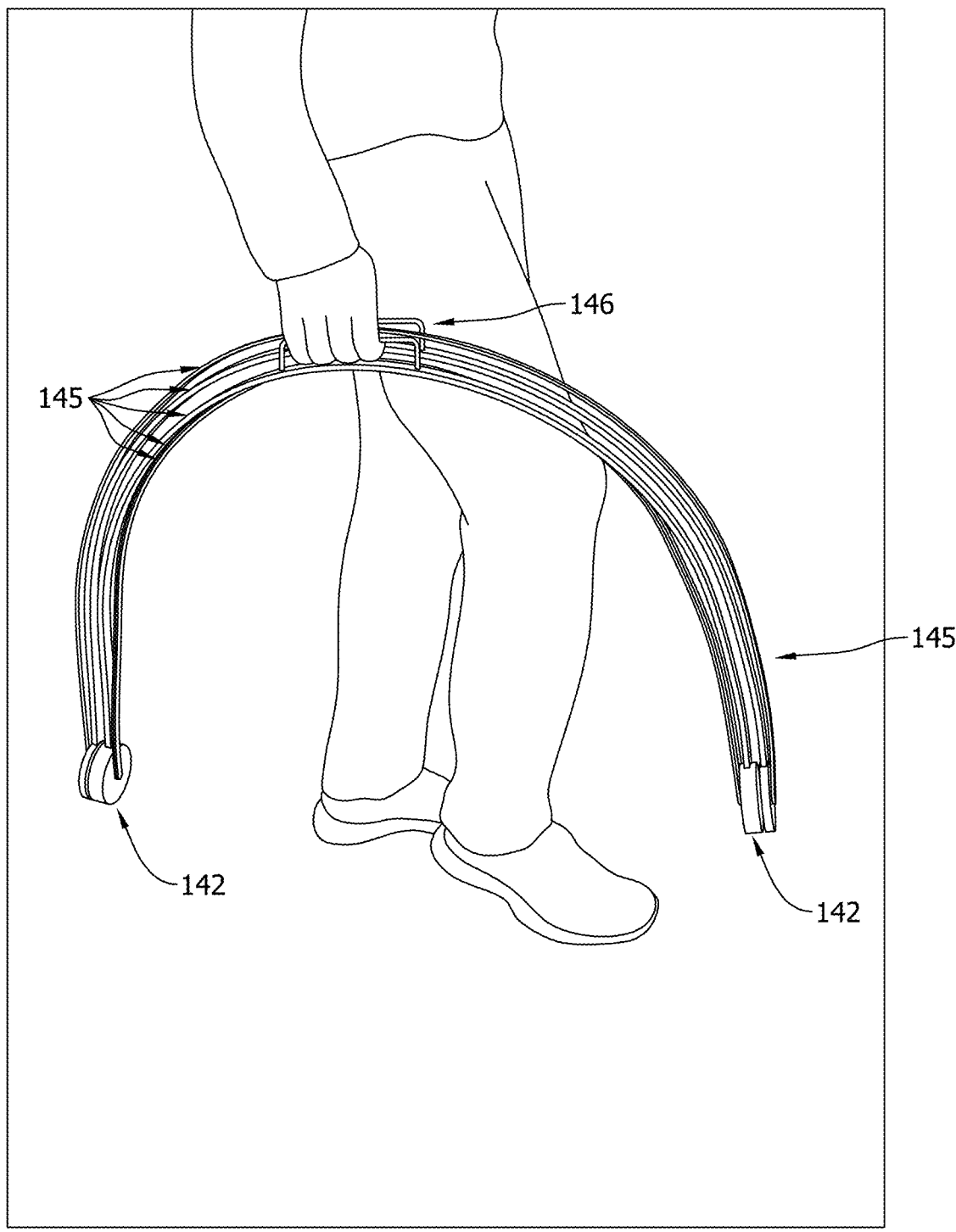
FIG. 14E a photograph of an example embodiment of the frame of a clamshell embodiment of the noise reducing system of the present invention in an open position, showing a person carrying the frame by its handles.
Figure 14F:
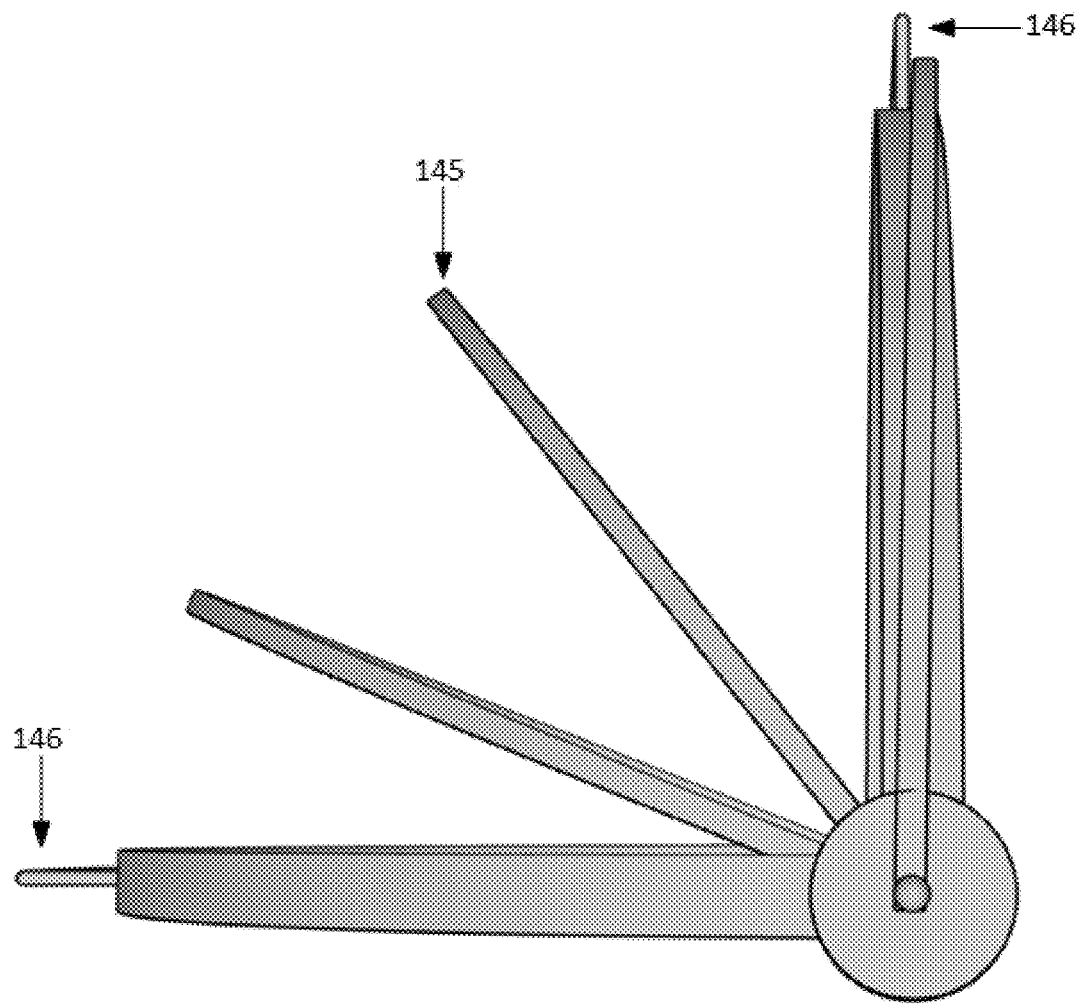
FIG. 14F a photograph of an example embodiment of the frame of a clamshell embodiment of the noise reducing system of the present invention in a partially closed position.
Figure 14G:
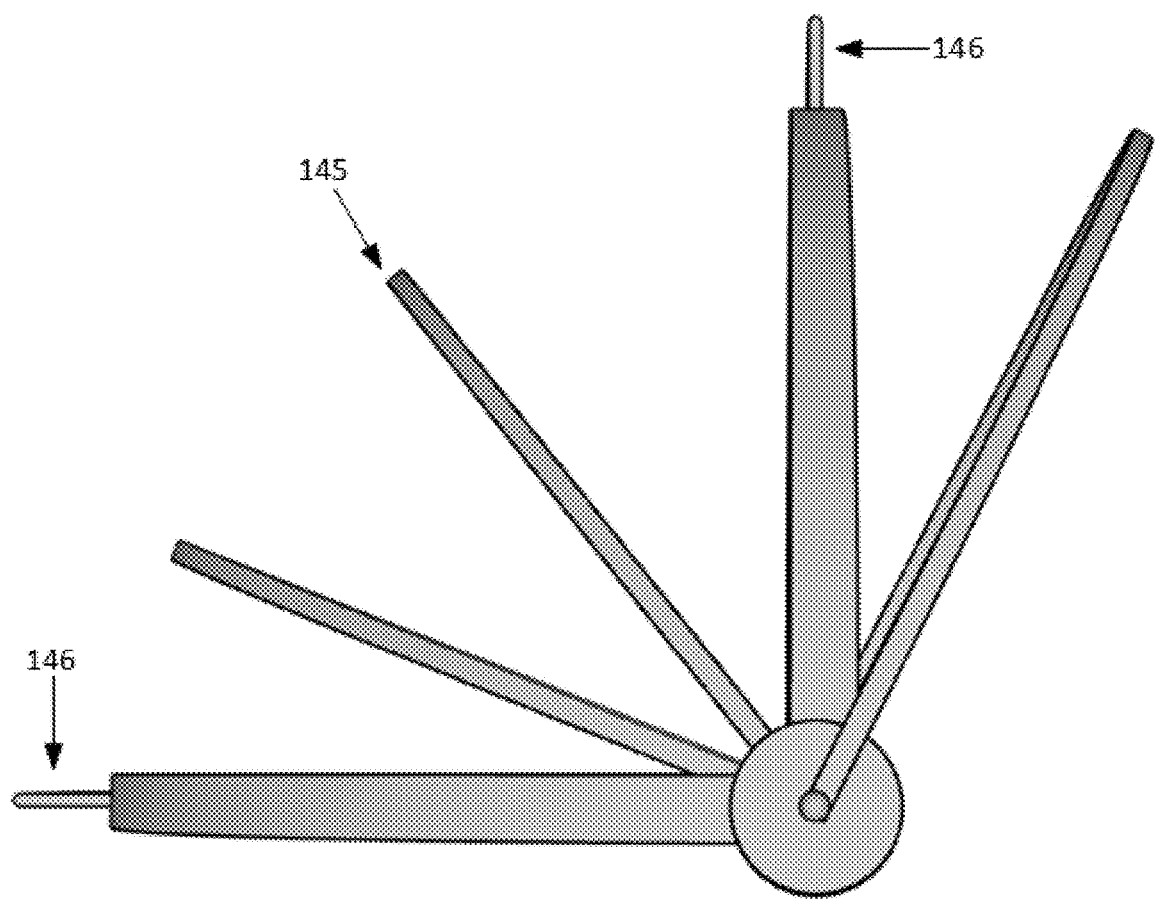
FIG. 14G a photograph of an example embodiment of the frame of a clamshell embodiment of the noise reducing system of the present invention in a fully closed position.
Figure 15A:
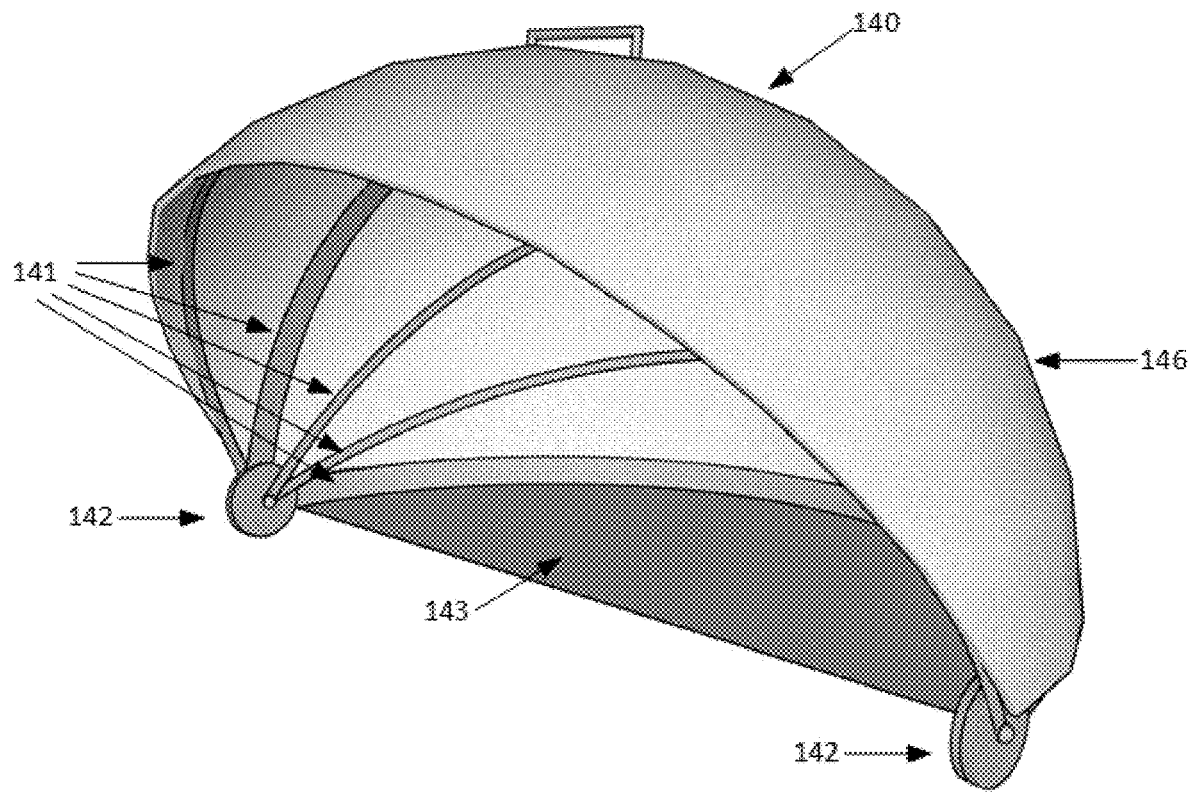
FIG. 15A depicts a perspective view of a clamshell embodiment of the noise reducing system of the present invention in a closed position.
Figure 15B:
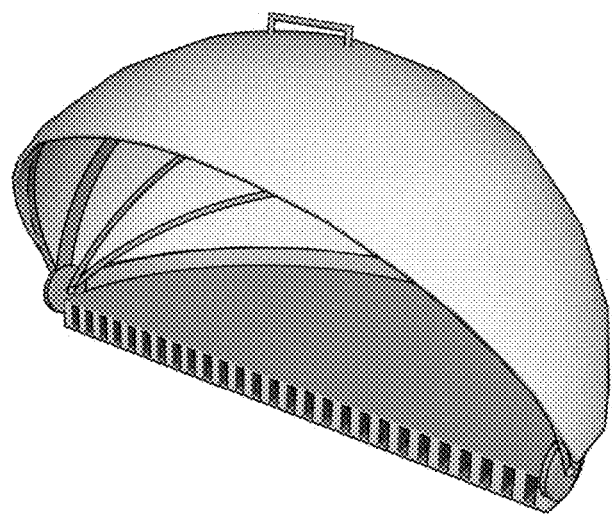
FIG. 15B a photograph of an example embodiment of a clamshell embodiment of the noise reducing system of the present invention in a closed position.
Figure 16:
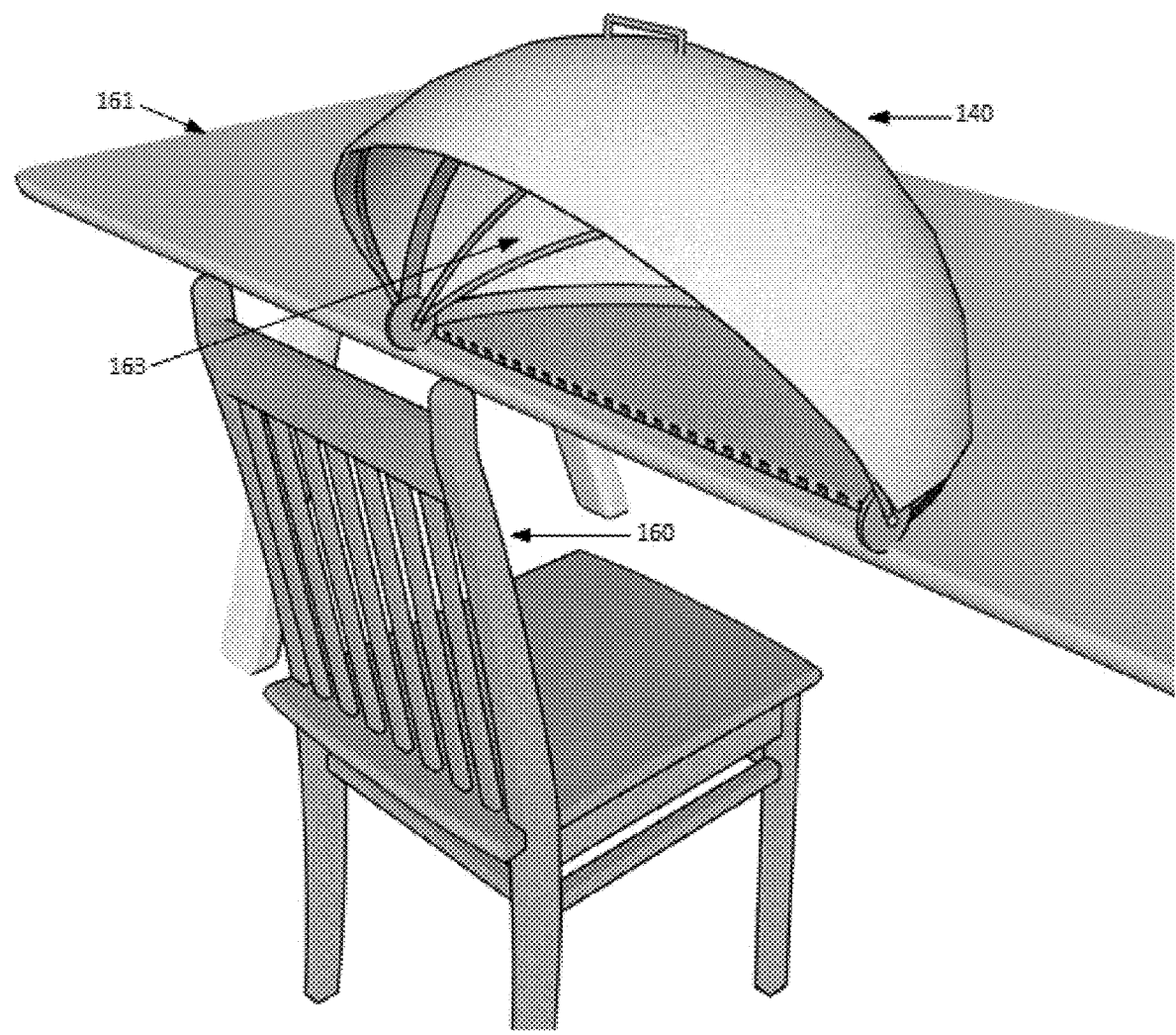
FIG. 16 depicts a perspective view of a clamshell embodiment of the noise reducing system of the present invention in a closed position showing a person using the invention in a seated position, such as at a desk, with the person's head inserted into the opening of the noise reducing system.

As depicted in FIG. 16, the user could put the user's head into the partial enclosure 140 on a desk or other surface 161 to rest the user's head 162 inserted into an opening 163 and take a nap on a desk, table, or other surface at which the user has been working or reading, or placed on a bed, floor, or other surface that the user would like to place their head or even a speakerphone to reduce the amount of noise that impinges on the ears of the user or area of auditory input. Another application is where an animal (such as a dog or baby) is sleeping in a bed and the portable clamshell could be placed in a full operational position so that the animal is not disturbed from sleep by intrusive noises, since when the animal wakes up and makes a noise (such as a dog barking, or a baby crying), it typically causes an additional disturbance to anyone nearby. Additionally, should the animal make noises, the sounds are reduced so as to not disturb those in proximity, such as when a person is on a conference call, a remote classroom, or other situation where such a disruptive noise is disturbing or problematic. A slightly larger version could be used on a desk to create quietude to the user, while working. In this application studies have shown that the reduction in noise when someone is working, studying, or reading not only would improve productivity to the user, but would help the user retain more informational content that has been read. The size of opening 163 may be adjusted by changing the position of the outermost rib 141 with respect to base 143. This can be easily performed by changing the relative positions of optional handles 146, or just holding the outermost rib and moving the rib to the desired location. Enclosure 140 may be adjusted from an open position (FIG. 14A), to a partially closed position (FIG. 14B), to a fully closed position (FIG. 14C).

Figure 17:
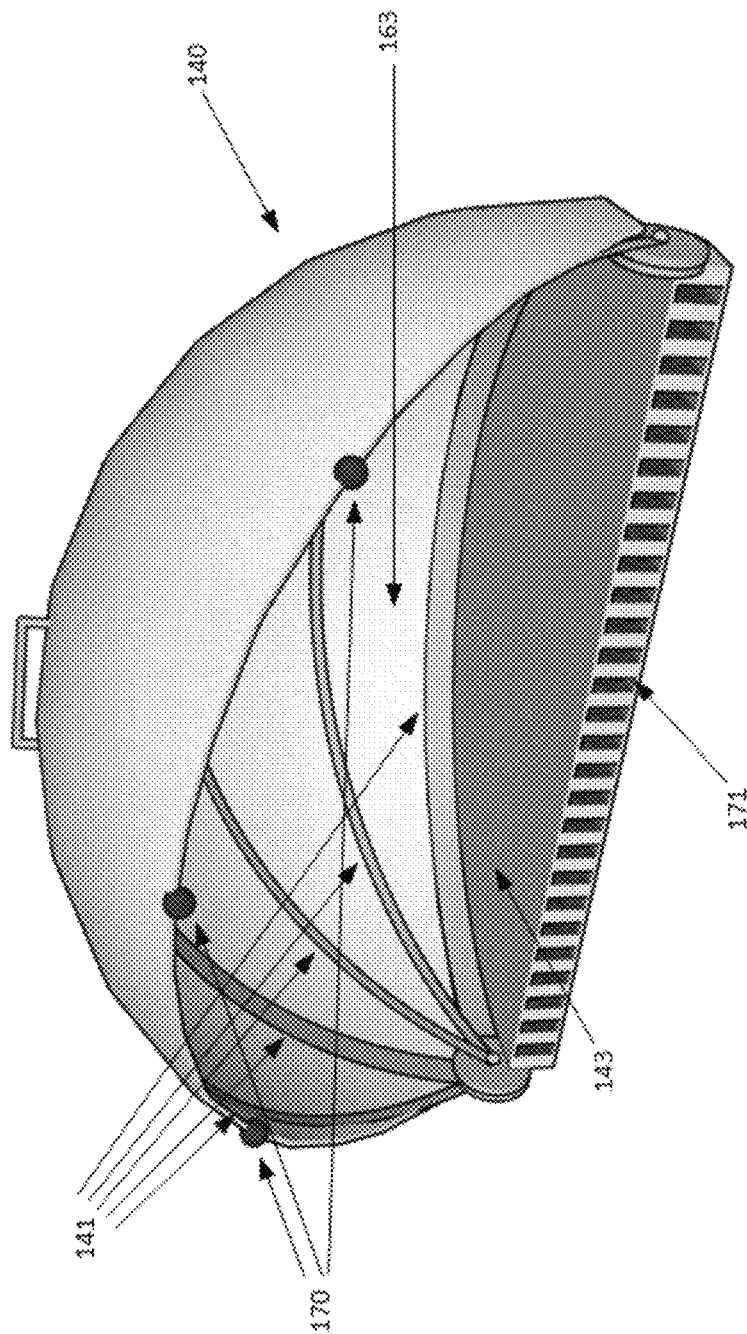
FIG. 17 depicts a perspective view of a clamshell embodiment of the noise reducing system of the present invention in a closed position showing speakers and/or microphones located along the opening of the noise reducing system.

Furthermore, as shown in FIG. 17, the edge of the opening 163 (which may be formed by a rib 141 or base 143) of the clamshell partial enclosure 140 can have the same adaptive sound masking or active noise cancelling capabilities using speakers and microphones 170 arranged at the opening of the enclosure as discussed above. Additionally, the enclosure 140 may include a filtered air system 171, which may be located in the base 143 of the enclosure 140. Also, the diffuser, grill, flow conduits, and associated nozzle can be part of the rib or enclosure in general. The air flow of the filtered air can additionally be fed into the clamshell enclosure 140, so as to create a white noise, pink noise, or adaptable sound masking. The quality and spectrum of the noise being determined by the application or price point of the product. That is, a less expensive model may have white noise created by a fan, but a more expensive model may have adaptable sound masking.

The noise reducing system may be configured to provide sounds of a heartbeat or similar sound the user identifies as soothing. That is, it may provide a familiar environment of light, sound, and smell to the user, which may allow the user's mind to relax more efficiently. The noise reducing system may also be configured to provide the sounds and vibration that mimics the sounds and vibrations of a womb. Filtered air system 171 may also be located at a position for, and configured for, providing aromatherapy. Additionally, filtered air system 171 may be configured to provide a familiar environment of smell to the user.

The clamshell design is intended to show the portability and ease of transport. A multitude of shapes can be used, such as a collapsible rectangle. Additionally, the focus of the above discussion is on helping in an office or sleeping, but this partial enclosure is equally important and applicable to someone with PTSD, whether the trauma was from a war situation or other stressful event, such as dealing with COVID.

As will be evident to persons skilled in the art, the foregoing detailed description, applications and figures are presented as examples of the invention, and that variations are contemplated that do not depart from the fair scope of the teachings and descriptions set forth in this disclosure.

What is claimed is:

1. A noise reducing system, comprising:
an acoustic partial enclosure constructed with a sheet of an acoustic material formed with one or more of a sound absorbing layer and a sound barrier layer to reduce noise going in or coming out of said partial enclosure from 23 dB to 35 dB;
said acoustic partial enclosure configured to block or inhibit unwanted sound from entering said acoustic partial enclosure from a source of said unwanted sound located proximate the partial enclosure, or from a source of the unwanted sound inside the partial enclosure even if the source is moving and as the moving source moves proximate the partial enclosure;
wherein the opening of the acoustic partial enclosure is sufficiently large to allow airflow, but small enough to reduce the number of direct noise paths entering or exiting the partial enclosure wherein the acoustic partial enclosure having one or more parts joined by a hinge, said acoustic partial enclosure having a closed position having a clamshell shape; wherein: said one or more parts include: one or more semicircular ribs joined at said hinges; and a semicircular base joined to said semicircular ribs at said hinges; and said sheet material joined at the perimeter of said base and at least one of said semicircular ribs; wherein one or more of said semicircular ribs and said base includes at least one handle, said handle extending through said sheet; and wherein: a first rib is joined to said base and includes a first handle; and a second rib is positioned distal to said first rib and includes a second handle.

2. The noise reducing system of claim 1, wherein the partial enclosure is formed with the at least one sound absorbing layer combined, layered, or integral with at least one sound barrier layer;
wherein the acoustic partial enclosure is positioned to inhibit noise emanating from a range of various sound sources and source positions from entering the partial enclosure, or where the sound source is inside the partial enclosure and even when the sound source position changes or is moving.

3. The noise reducing system of claim 1, wherein the sound absorbing layer comprises a nonwoven sound absorbing material.

4. The noise reducing system of claim 2 wherein the sound barrier layer comprises a sound barrier formed of loaded vinyl.

5. The noise reducing system of claim 1, wherein the acoustic partial enclosure is collapsible.

6. The noise reducing system of claim 1, wherein the sheet includes a finishing fabric on one or more of one or more of an inside surface and an outside surface.

7. The noise reducing system of claim 1 wherein the enclosure may be opened from a first open position to a second closed position, wherein the second closed position may be adjusted to reduce the noise entering or exiting to bring a level of quietude.

8. The noise reduction system of claim 1, wherein the acoustic partial enclosure at least partially covers the unwanted sound source.

9. The noise reduction system of claim 1, wherein the acoustic partial enclosure is sized to at least partially cover an animal to acoustically shield the animal from the unwanted sound source.

10. The noise reduction system of claim 1, further including a base formed of one or more of a fabric, a cushion, or a vibration pad.

11. The noise reduction system of claim 10, wherein the base may be formed of a high durometer pad.

12. The noise reducing system of claim 1, further including:
   one or more third ribs positioned intermediate to said first rib and said second rib; and
   a fourth rib positioned distal to said second rib and forming, with an edge of said base, said opening.

13. The noise reducing system of claim 12, wherein, in an open position:
   said one or more third ribs nest inside said first rib; and
   said second rib nests inside said fourth rib.

\* \* \* \* \*